United States Patent [19]

Minagawa et al.

[11] 3,997,551
[45] Dec. 14, 1976

[54] 3-SALICYLAMIDO-S-TRIAZOLES

[75] Inventors: Motonobu Minagawa, Koshigaya; Mitsuo Akutsu; Kenichi Nakagawa, both of Tokyo, all of Japan

[73] Assignee: Argus Chemical Corporation, Brooklyn, N.Y.

[22] Filed: Dec. 20, 1974

[21] Appl. No.: 534,988

Related U.S. Application Data

[62] Division of Ser. No. 473,526, May 28, 1974, Pat. No. 3,963,982, which is a division of Ser. No. 211,647, Dec. 23, 1971, Pat. No. 3,849,370.

[30] Foreign Application Priority Data

Dec. 30, 1970  Japan .......................... 46-122270

[52] U.S. Cl. .................. 260/308 R; 260/294.8 C; 260/294.8 E; 260/294.8 G; 260/295 K; 260/295 E; 260/295 AM
[51] Int. Cl.$^2$ .............. C07D 249/10; C07D 401/04
[58] Field of Search ................ 260/308 R, 294.8 C, 260/294.8 E, 294.8 G, 295 K, 295 E, 295 AM

[56] References Cited

UNITED STATES PATENTS 2,953,491   9/1960   Hardy et al. .................. 260/308 R

OTHER PUBLICATIONS

Jensen et al., Acta Chem. Scand., vol. 6, pp. 166–171 (1952).

*Primary Examiner*—Alton D. Rollins

[57] ABSTRACT

3-salicylamido and 3-benzosalicylamido-1,2,4-triazoles are provided which are useful in the enhancement of the resistances of olefin polymers to heavy metal-catalyzed oxidative deterioration.

Stabilizer compositions consisting essentially of at least one olefin polymer stabilizer and such amidotriazoles; olefin polymer compositions, such as propylene polymer compositions, containing such amidotriazoles and a process for enhancing the resistance of olefin polymers to copper-catalyzed degradation by incorporation of such amidotriazoles or such stabilizer compositions are also provided.

6 Claims, No Drawings

3,997,551

3-SALICYLAMIDO-S-TRIAZOLES

This is a division of application Ser. No. 473,526 filed May 28, 1974, now U.S. Pat. No. 3,963,982, which in turn is a division of Ser. No. 211,647 filed Dec. 23, 1971 now U.S. Pat. No. 3,849,370, patented Nov. 19, 1974.

Polypropylene is a tough, hard, relatively flexible, high-melting polymeric material, and thus has a number of important applications, such as, for example, as electrical insulation for copper wires and cables. However, in several respects the stability of polypropylene leaves much to be desired. The polymer shows a tendency to decrease rapidly in melt viscosity and then to become brittle when kept at elevated temperatures for the time required in milling, calendering, extrusion, injection molding, and fiber-forming equipment. This deterioration is particularly serious when the polymers are worked in a molten state in the presence of oxygen, for example, air. It is known in the art that degradation in one or more physical properties of polypropylene due to heat can be inhibited by the incorporation of a number of well known thermal antioxidants, including hindered phenols, secondary aromatic amines, organic phosphites, and thiodipropionic acid esters.

A special problem is presented when the polypropylene is contaminated by or is used in contact with a heavy metal such as copper. Thus, polypropylene employed as insulation for copper wires and cables becomes useless after a few months. In fact, it has been found that oxidative degradation of polypropylene occurs at an extremely rapid rate in the presence of copper, even when the polymer contains effective antioxidants. Hanson et al, *Journal of Polymer Science*, Part A, 2, 587–600 (1964), report at page 589 that "The catalytic effect of copper on the thermal oxidation of polypropylene is not as drastic in the absence of antioxidants as it is in their presence". (Emphasis added). Where polypropylene contains antioxidant, in the presence of copper "the rate of oxidation becomes rapid and constant after a drastically shortened induction period compared with that obtained in the absence of copper". (page 590). "The induction period in oxygen at 140° C for polypropylene stabilized by the addition of 0.5 weight percent of 4,4'-thiobis (3-methyl-6-tert-butylphenol) is decreased from about 400 hours to 40 hours by the presence of copper. Similar 90% losses in the effectiveness of this antioxidant in the presence of copper have been observed over a range of temperatures". (page 591).

To inhibit copper-catalyzed oxidation, conventional copper chelating agents and metal deactivators have been added to polypropylene compositions containing thermal antioxidants. As reported by Hansen et al, supra, at page 593, "All of these materials were found to be unsatisfactory for a variety of reasons. Most of them did not diminish the catalytic activity of copper and copper compounds. Some actually accelerated the already rapid copper-catalyzed oxidation of polypropylene, and might be useful in other reactions where oxidation is sought rather than avoided. The best of the conventional deactivators (for example, N,N'-di-β-naphthyl-p-phenylenediamine) were only sightly effective in curtailing the catalytic activity of copper." It is also reported that other conventional and commercial metal inhibitors or deactivators, such as ethylenediamine tetraacetic acid and its salts, 2,2'-bipyridyl, 8-quinolinol, N,N'disalicylidene-1,2-propanediamine, and benzimidazole, either were ineffective or only slightly effective, and usually had other disadvantages, including instability, incompatibility, water-solubility, volatility, formation of highly colored products, and reaction with other components of the polypropylene composition.

A number of compounds have been suggested, for use in suppressing copper-catalyzed oxidation of polypropylene. Hansen et al, supra, and British Pat. No. 974,274, to Western Electric Company, Inc., recommended oxamide and compounds derived from oxamide which contain the radical

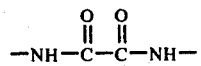

for inhibiting copper-catalyzed oxidation of polypropylene. Hansen et al reported that polypropylene compositions containing 0.5% by weight antioxidant and 0.5% by weight oxamide or substituted oxamide retained between 30 to 80% of the effectiveness of the antioxidant in the presence of copper, while when oxamide or its derivatives were not used, only between 1 and about 15% of the normal induction period for an antioxidant was observed.

Hansen et al, *Polymer Engineering and Science*, Vol. 5, October, 1965, pages 223 to 226, reported that nitrobenzohydrazides, oxalyldihydrazide and its derivatives, triazines, triazoles, triazolines, and tetrazoles, are effective copper inhibitors. However, many of these compounds destroy the effectiveness of antioxidants, such as N-phenyl-2-naphthylamine, 4,4'-thiobis(3-methyl-6-tertiary-butylphenol) and 6,6'-di-tert-butyl-4,4'-bis-o-cresol.

A number of other compounds which are apparently useful as copper deactivators and inhibit copper-catalyzed oxidation of polypropylene are known. U.S. Pat. No. 3,110,096 to Dexter discloses compounds of the formula.

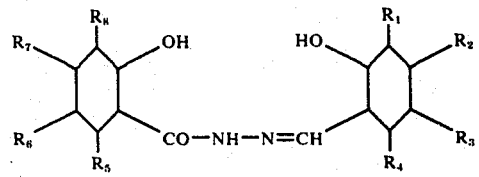

wherein the R radicals are hydrogen, alkyl, alkoxy or phenyl. Dexter prefers N'salicylidene-N'-salicylhydrazide.

U.S. Pat. No. 3,117,104 to Bown et al discloses oxaldihydrazides having the formula

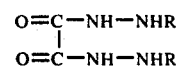

where R is an alkyl of up to 16 carbon atoms, monoaryl or naphthenyl, having from five to 12 carbon atoms. Such compounds are shown to reduce the stabilizing effectiveness of dilauryl thiodipropionate in the presence of copper by about 75%.

British Pat. No. 994,116 to Shell teaches that stabilizer combinations which contain (a) an organic sulfur compound of the type $R_1\text{-}S_xR_2$, wherein $x$ is an integer of up to 2 and $R_1$ and $R_2$ are alkyl, aralkyl, or cycloalkyl, having from eight to 25 carbon atoms and (b) a polynuclear polyphenol consisting of a benzene ring substituted with $n$ 3,5-dialkyl-4-hydroxybenzyl groups wherein $n$ is 3 or 4, are effective in protecting alkene polymers, prepared by a low-pressure polymerization process, such as the Ziegler process, against deterioration caused by light, heat and oxygen. However, it is stated that these stabilizer compositions are incapable of protecting the polymer effectively against deterioration in properties caused by contact between copper and polymer. In discussing the prior art, it is indicated that British Pat. No. 890,761 discloses stabilizer combinations offering protection against deterioration caused by contact between copper and polymer, viz. a combination comprising a diester of a beta-thiodipropionic acid and a bis-phenol obtained by the condensation reaction of 1 mol of saturated aldehyde or ketone having 4 to 6 carbon atoms or of sulphur dichloride and 2 mols of a phenol having a non-reactive ortho substituent and a non-substituted para ring carbon atom. British Pat. No. 961,931 also discloses the incorporation of a diester of beta-thiodipropionic acid in combination with a certain trisphenolic compound which is obtained by the condensation reaction of either 1 mol of unsaturated aldehyde or ketone and 3 mols of phenol having a non-reactive ortho or para hydrocarbon substituent, or 1 mol of hydroxyaryl-substituted saturated aldehyde or ketone and 2 mols of phenol having a non-reactive ortho or para hydrocarbon substituent, into polymers in order to stabilize the latter against deterioration caused by contact with copper.

However, British Pat. No. 994,116 states at page 2, column 1, that "the stability of such polymer compositions containing the relevant stabilizer combinations comprising these diesters plus said bis- or trisphenolic compounds leaves much to be desired when these compositions — whether or not in contact with copper — are exposed to elevated temperatures. This gives rise to serious difficulties during the manufacture of the insulated electric conductors from which the insulating material consists of such stabilized compositions, since these are manufactured by coating the conductor with heat-plastified or molten polymer material. As is known, high temperatures, generally higher than 130° C, are used when such coatings are applied. Moreover, electric conductors coated with such stabilized compositions are, of course, not very suitable for use at elevated temperatures."

British Pat. No. 984,116 suggests that this problem can be met by incorporating in the polymer together with the organic sulfur compound and a polynuclear polyphenol, a bis- or trisphenollic compound obtained by the reaction of either a saturated or unsaturated aldehyde or ketone, of sulfur dichloride, and a phenol having at least one ortho-ring carbon atom bound to a secondary or tertiary alkyl group. Apparently, the bis- or trisphenolic compound when employed with the aove stabilizers protects the polymer against deterioration caused by contact between copper and polymer even when the polymer is exposed to elevated temperatures, such as 150° C and above.

British Pat. No. 951,933 to Imperial Chemical Industries, Limited, discusses the problem of protection of polyolefins containing phenolic antioxidants against copper-catalysed oxidative deterioration. The phenolic compounds are said to be especially effective as antioxidants when they are used in conjunction with an organic sulfur compound having a molecular weight of at least 250. The patent provides a polymeric composition suitable for use in close contact with copper, which composition comprises a solid polymer of propylene, particularly isotactic polypropylene, a phenolic antioxidant, and non-volatile primary or secondary aromatic or aliphaic amino compounds, the secondary aromatic amino compounds having at least one nitrogen atom to which is attached not more than one aryl group. These amines are, in general, not those which are generally preferred as antioxidants in rubber and plastics. Many of these amino compounds, e.g., p-aminoacetanilide, do not confer any extra protection on polypropylene stabilized with mixtures of phenolic compounds and sulphur compounds in the absence of copper and do not prevent the degradation of polypropylene in the presence of copper when they are used in the absence of the phenolic stabilizer. The aliphatic amino compounds usually cause less staining than the aromatic amino compounds, the acid hydrazides being particularly good in this respect.

U.S. Pat. No. 3,367,907 to Hansen teaches polyolefin compositions stabilized against degradation accelerated by the presence of copper. There is incorporated in the polymer an antioxidant, such as a phenol, and a "copper inhibitor", which can be any azimidobenzene containing the radical:

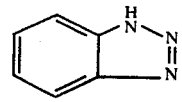

or any corresponding benzotriazine characterized by the structure

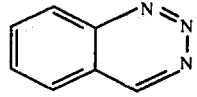

In accordance with the instant invention, 3-salicylamido and 3-benzosalicylamido-1,2,4-triazoles are provided, useful in olefin polymer compositions, such as polypropylene, containing one or more olefin polymer stabilizers, which come in contact with heavy metals such as copper.

In the presence of such amidotriazoles, the usual catalytic effect of heavy metals such as copper on the rate of degradation of the olefin polymer is not observed, and instead, the olefin polymer displays a resistance to such degradation, enhanced by the usual olefin polymer stabilizer or stabilizer system, that is virtually as high as though he heavy metal were not present. This is especially surprising in view of the fact that heavy metals substantially reduce the effectiveness of most commercially available antioxidants in olefin polymers, even when so called conventional "metal deactivators" are incorporated in the polymer.

Further in accordnce with the instant invention, stabilizer systems for olefin polymers are provided consisting essentially of at least one olefin polymer stabilizer and 3-salicylamido and 3-benzosalicylamido-1,2,4-triazoles of the invention, to substantially reduce and in many cases overcome any deleterious effect of heavy metal on the olefin polymer stabilizer or olefin polymer.

In addition, in accordance with the invention olefin polymer compositions are provided, such as propylene polymer compositions, consisting essentially of olefin polymer and at least one amidotriazole of the invention.

Olefin polymer compositions of the invention containing these amidotriazoles can be used in contact with heavy metal such as copper and can be combined with the usual olefin polymer stabilizers to enhance resistance to oxidative deterioration. Consequently, such olefin polymer compositions can include, optionally, at least one olefin polymer stabilizer.

Further, in accordance with the instant invention, a process for enhancing the resistance of olefin polymers, such as propylene polymers, to heavy metal-catalyzed oxidative deterioration is provided, which comprises incorporating in the olefin polymer at least one amidotriazole as defined herein, and optionally, at least one olefin polymer stabilizer.

The olefin polymer stabilizers which can be employed in the invention include, for instance, phenols, organic phosphites, thiodipropionic acid esters, polyvalent metal salts of organic acids, and hydrocarbon sulfides and polysulfies, and conventional olefin polymer light stabilizers as will be seen hereinafter.

The 3-salicylamido and 3-benzosalicylamido-1,2,4-triazoles in accordance with the invention have the following structure:

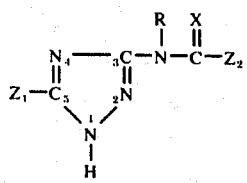

wherein:
a. R is selected from the group consisting of hydrogen and alkyl having from one to four carbon aoms;
b. $Z_1$ is selected from the group consisting of hydrogen, alkyl having from one to about 18 carbon atoms; aryl and alkylaryl having from six to about 18 carbon atoms; alkylenealkoxy and alkylenearyloxy having from two to about 18 carbon atoms and nitrogen-containing heterocyclic rings having from four to five ring carbon atoms and one to two ring nitrogen atoms;

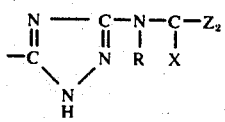

and

in which A is alkylene having from one to about eight carbon atoms;

c. X is selected from the group consisting of oxygen and sulfur;
d. $Z_2$ is a benzene or naphthalene ring substituted by from one to two $R_1$ groups and from zero to two $R_2$ groups, and
  i. $R_1$ is selected from the group consisting of OH, SH, $SR_3$ (where $R_2$ is selected from the the group consisting of alkyl and alkylene carboxyalkyl having from one to four carbon atoms), and

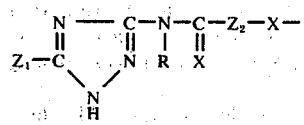

(where X is as in (c) above) and at least one $R_1$ is in the ortho position);
  ii. $R_2$ is selected from the group consisting of alkyl phenyl, alkyl phenyl, alkoxy, acyl, acyloxy, phenoxy and alkyl phenoxy having from one to about 18 carbon atoms, halogen and amino and

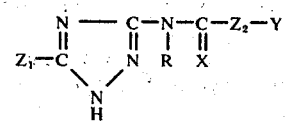

where Y is selected from the group consisting of oxygen, sulfur,

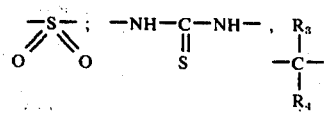

(where $R_3$ and $R_4$ are selected fron the group consisting of hydrogen and alkyl having from one to three carbon atoms), provided that there are at most two 1,2,4-tri-azole groups in the molecule.

When $Z_2$ is a benzene ring, the compounds take the form;

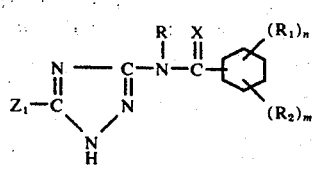

where n is 1 or 2 and m is 0, 1 or 2.
When $Z_2$ is a naphthalene ring, the compounds take the form:

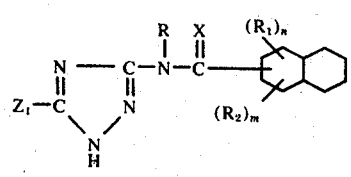

where n and m are as in II.
Exemplary R and $R_2$, $R_3$, $R_4$, $R_5$, and $Z_1$ alkyl groups include methyl, ethyl, propyl, isopropyl, n-butyl, secbutyl, tert-butyl, pentyl, hexyl, heptyl, n-octyl, iso-octyl, nonyl, decyl, undecyl, dodecyl, myristyl, palmityl and stearyl.

Exemplary $Z_1$ alkylaryl groups include tolyl, methyl, naphthyl, xylyl, mesityl, ethyl phenyl, dodecyl phenyl, nonyl phenyl, and hexyl phenyl.

Exemplary A alkylene groups include ethylene, propylene, hexylene, octylene, butylidene, butylene, ethylidene, propylidene, isopropylidene, isobutylidene, and pentylene.

Exemplary SR groups are thiomethyl, thioethyl, thiopropyl, and thiobutyl, thioethylene carboxyethyl, thiomethylene carboxymethyl, and thiopropylene carboxymethyl.

Exemplary halogen are fluorine and chlorine.

Exemplary $R_2$ acyl and acyloxy are acetyl, propionyl, butyryl, acetyloxy, propionyloxy and butyryloxy, myristoyl, myristoyloxy, stearoyl, stearoyloxy, dodecoyl and dodecoyloxy.

Exemplary $Z_1$ alkylenealkoxy and alkylenearyloxy include ethyleneoxyethyl, methyleneoxybutyl, ethyleneoxypropyl methylene oxypalmityl, propylene oxyhexyl, methylene oxyphenyl, ethylene oxybenzyl, ethylene oxyxylyl, propylene oxymesityl, and ethylene oxyphenylethyl.

Exemplary $Z_1$ heterocyclic include pyridyl, piperidyl, pyrrolyl, and pyrazolyl, pyrimidyl, pyrazinyl and pyridazinyl.

Exemplary $Z_1$ aryl include phenyl and naphthyl.

The following Examples illustrate the preparation of the amidotriazoles of the invention:

A.     Melting Point
       316–321° C.

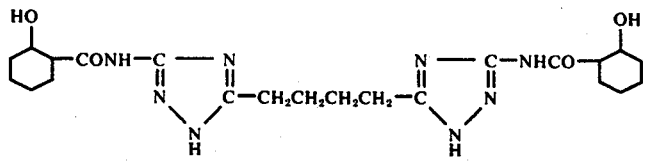

5.5 parts of 1, 4-bis-(5-(3-amino-1,2,4-triazole)) butane and 20.0 parts of phenyl salicylate were reacted at 180° C for 4 hrs., and 100 vol. parts of methanol were added and refluxed for 1 hr. 8.0 parts of white powder was recovered by filtration. (mp. = 316° – 321° C)

| Elemental Analysis: | C% | H% | N% |
|---|---|---|---|
| (Calc.) | 56.82 (57.12) | 4.90 (4.79) | 24.36 (24.23) |

B.     Melting Point
       331–336° C.

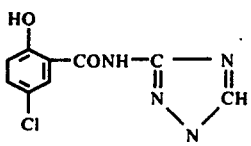

3.6 parts of 3-amino-1,2,4-triazole and 10.4 parts of 5-chlorosalicylic acid phenyl ester were reacted at 170° C for 1 hr., and 100 vol. parts of methanol were added and refluxed. 7.3 parts of white crystalline powder were recovered by filtration. (mp. = 331°–336° C)

| Elemental Analysis: | C% | H% | N% |
|---|---|---|---|
| (Calc.) | 45.10 (45.29) | 3.00 (2.96) | 23.28 (23.48) |

C.     Melting Point
       313–320° C.

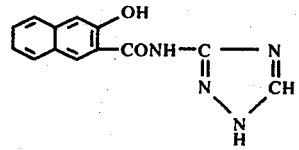

13.2 parts of 2-hydroxy-3-naphthoic acid phenyl ester and 4.3 parts of 3-amino-1,2,4-triazole were reacted at 140° C. for 3 hrs. After heating with 50 parts of methanol, 1.5 parts of colorless powder was obtained after filtration and drying.

| Elemental Analysis: | C% | H% | N% |
|---|---|---|---|
| (Calc.) | 61.24 (61.41) | 3.99 (3.96) | 22.00 (22.04) |

D.     Melting Point
       >250° C.

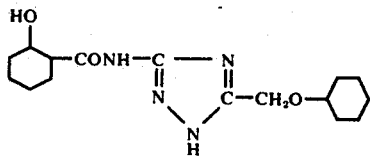

7.8 parts of salicyclic acid chloride was added dropwise into a mixture of 9.5 parts of 5-phenyloxymethyl-3-amino-1,2,4-triazole and 40 parts by volume of xylene at room temperature, and reacted at 130° C. for 3 hrs. After neutralization with sodium bicarbonate and heating with 100 parts by volume methanol, 12.1 parts of white powder was obtained.

| Elemental Analysis: | C% | H% | N% |
|---|---|---|---|
| (Calc.) | 61.90 (61.92) | 4.59 (4.55) | 18.12 (18.06) |

E.     Melting Point
       294–302° C.

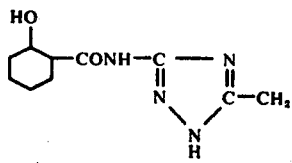

A mixture of 9.7 parts of 3-amino-5-methyl-1,2,4-triazole, 21.4 parts of phenyl salicylate and 50 parts by volume of xylene were refluxed for 3 hours. After heating with 100 parts by volume of methanol, 9.9 parts of white powder was obtained.

| Elemental Analysis: | C% | H% | N% |
|---|---|---|---|
| (Calc.) | 54.99 (55.03) | 4.70 (4.62) | 26.01 (25.71) |

F. Melting Point 300° C.

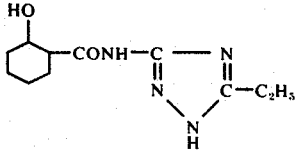

4.2 parts of 3-amino-5-ethyl-1,2,4-triazole and 11.5 parts of phenyl gentisate were added to 30 parts of ethylene-glycol dimethylether, and reacted at 150° C. for 3 hours. Then solvent and phenol were eliminated, and the residue heated with methanol. After filtration and drying, 6.7 parts of pale yellow powder was obtained.

10.7 parts of phenyl salicylate and 4.7 parts of 3-amino-1,2,4-triazole were reacted at 160° C. for 1 hour. 40 parts by volume of xylene were added and refluxed for 3 hours. After heating with methanol, 5.5 parts of white powder was obtained.

| Elemental Analysis: | C% | H% | N% |
|---|---|---|---|
| (Calc.) | 52.82 (52.94) | 3.99 (3.95) | 27.55 (27.45) |

H. Melting Point 250° C

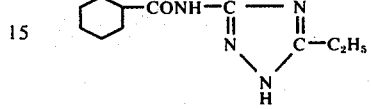

5.5 parts of 5-ethyl-3-amino-1,2,4-triazole and 13.8 parts of para-nitrophenyl 2-mercaptobenzoate were reacted at 150° C. for 3 hours. After heating with methanol, 6.3 parts of very slight yellow powder was obtained.

| Elemental Analysis: | C% | H% | N% | S% |
|---|---|---|---|---|
| (Calc.) | 53.02 (53.22) | 4.91 (4.87) | 22.87 (22.57) | 12.78 (12.89) |

I. Melting Point 300° C.

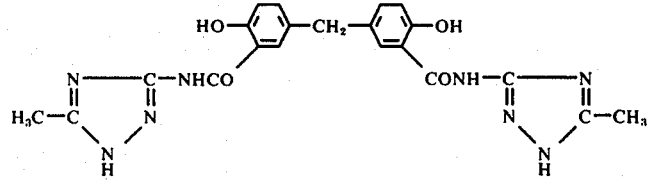

13.3 parts of 5,5-methylene-bis-salicylic-acid-para-nitrophenyl ester, 5.0 parts of 5-methyl-3-amino-1,2,4-triazole and 40 vol. parts of dimethylformamide were reacted at 145° C. for 4 hours. Solvent was eliminated and heat-treated with methanol. 8.4 parts of white powder was gained after filtration and drying.

| Elemental Analysis: | C% | H% | N% |
|---|---|---|---|
| (Calc.) | 53.27 (53.22) | 4.89 (4.87) | 22.61 (22.57) |

G. Melting Point 290–300° C.

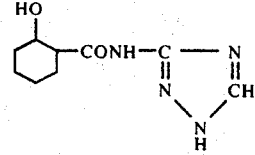

| Elemental Analysis: | C% | H% | N% |
|---|---|---|---|
| (Calc.) | 56.61 (56.24) | 4.61 (4.50) | 24.80 (24.99) |

J. The following additional compounds have also been prepared, using one of the above procedures:

Melting Point

| -continued | | | | |
|---|---|---|---|---|
| Elemental Analysis: | C% | H% | N% | |

[Structure: 2-hydroxy-5-chloro-cyclohexanecarboxamide linked to 1,2,4-triazole] — 331–336° C.

[Structure: 2,5-dihydroxy-cyclohexanecarboxamide linked to 1,2,4-triazole] — >300° C.

[Structure: 2-hydroxy-5-butoxy-benzamide linked to 1,2,4-triazole] — 280–290° C.

[Structure: 2-hydroxy-5-methyl-benzamide linked to 1,2,4-triazole] — 320–228° C.

[Structure: 2,5-dihydroxy-benzamide linked to 1,2,4-triazole] — 300° C.

[Structure: salicylamide linked to 3-octyl-1,2,4-triazole] — 276–290° C.

[Structure: salicylamide linked to 3-(2-ethoxyethyl)-1,2,4-triazole] — 283–299° C.

[Structure: salicylamide linked to 3-(2-pyridyl)-1,2,4-triazole] — 250° C. decomposed

[Structure: thiosalicylamide linked to 3-phenyl-1,2,4-triazole] — 200° C. decomposed

[Structure: thiosalicylamide linked to 3-methyl-1,2,4-triazole] — 200° C. decomposed -continued
| Elemental Analysis: | C% | H% | N% |
|---|---|---|---|
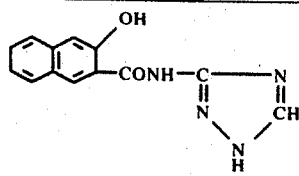
313–320 C.
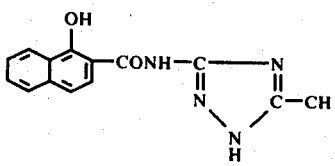
315–330 C.
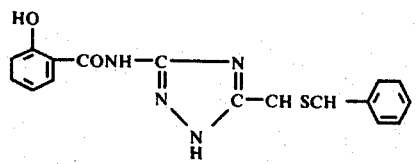
300 C.
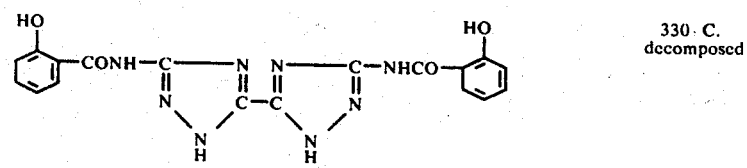
330 C. decomposed
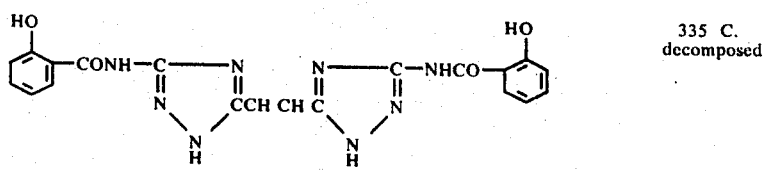
335 C. decomposed
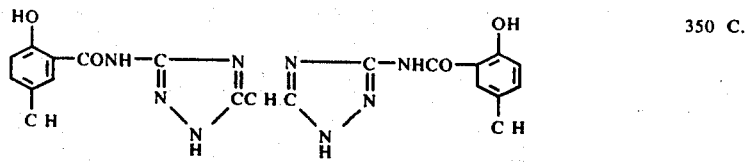
350 C.
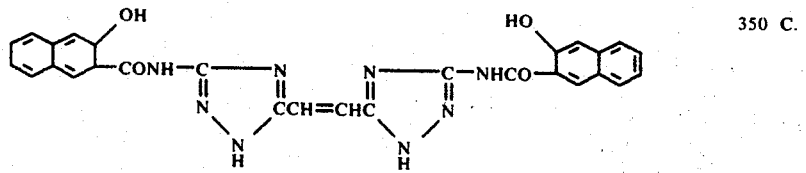
350 C.
200 C. decomposed -continued

| Elemental Analysis: | C% | H% | N% |
|---|---|---|---|

[Structure 1] >230° C. decomposed

[Structure 2] >350° C.

[Structure 3] >350° C.

[Structure 4] >250° C. decomposed

[Structure 5] 250° C. decomposed

[Structure 6] 230° C. decomposed

The stabilizer system of the invention comprises one or more compounds of the invention in combination with at least one olefin polymer stabilizer, and preferably, two or more such stabilizers. It is well known that in the case of olefin polymers, combinations of stabilizers can be complementary, and can enhance the resistance of the olefin polymer to oxidative deterioration. Such enhanced stabilizing effectiveness when present in the olefin polymer stabilizer combination continues to be evidenced in the presence of the stabilizer system of the invention.

Stabilizer systems of the invention comprising a compound of the invention and an olefin polymer stabilizer can be formulated and marketed as such, ready for use by the converter of the olefin polymer into useful products.

A variety of olefin polymer stabilizers can be employed of which the following are exemplary.

The organic phosphite can be any organic phosphite having one or more organic radicals attached to phosphorus through oxygen. These radicals can be monovalent radicals in the case of the triphosphites, diphosphites and monophosphites, which can be defined by the formula:

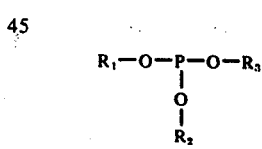

in which $R_1$, $R_2$ and $R_3$ are selected from the group consisting of hydrogen, alkyl, alkenyl, aryl, alkaryl, aralkyl, and cycloalkyl groups having from one to about 30 carbon atoms.

Also included are the organic phosphites having a bivalent organic radical forming a heterocyclic ring with the phosphorus of the type:

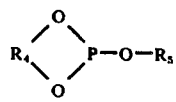

in which $R_4$ is a bivalent organic radical selected from the group consisting of alkylene, arylene, aralkylene, alkarylene and cyclo-alkylene radicals having from two to about 30 carbon atoms, and $R_5$ is a monovalent organic radical as defined above in the case of $R_1$, $R_2$ and $R_3$.

Also useful in the compositions of the invention are mixed heterocyclic-open chain phosphites of the type:

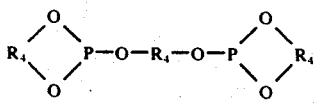

More complex phosphites are formed from trivalent organic radicals, of the type:

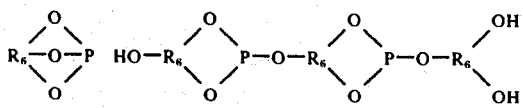

in which $R_6$ is a trivalent organic radical or any of the types of $R_1$ to $R_5$, inclusive, as defined above.

A particularly useful class of complex phosphite are the tetraoxadiphosphaspiro undecanes of the formula

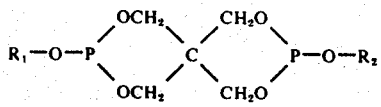

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl.

An expecially preferred class of organic phosphites have a bicyclic aromatic group attached to phosphorus through oxygen, with no or one or more phenolic hydroxyl groups on either or both of the aromatic rings. These phosphites are characterized by the formula:

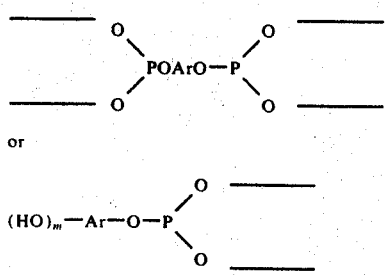

in which Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms. Z can also be hydrogen, and can include additional by-cyclic aromatic groups of the type $(HO)_m$-Ar.

The term "organic phosphite" as used herein is inclusive of the above-described mono-, di- and triphosphites. Usually, the phosphite will not have more than about 60 carbon atoms.

Exemplary are monophenyl di -2-ethylhexyl phosphite, diphenyl mono-2-ethylhexyl phosphite, di-isooctyl monotolyl phosphite, tri-2-ethylhexyl phosphite, phenyl dicylohexyl phosphite, phenyl diethyl phosphite, triphenyl phosphite, tricresyl phosphite, tri(-dimethylphenyl) phosphite, trioctadecyl phosphite, triisooctyl phosphite, tridodecyl phosphite, isooctyl diphenyl phosphite, diisooctyl phenyl phosphite, tri(t-octylphenyl) phosphite, tri(t-nonylphenyl) phosphite, benzyl methyl isopropyl phosphite, butyl dicresyl phosphite, isooctyl di(octylphenyl) phosphite, di(2-ethylhexyl) (isooctylphenyl) phosphite, tri(2-cyclohexylphenyl) phosphite, tri-α-naphthyl phosphite, tri(-phenylphenyl) phosphite, tri(2-phenyl ethyl) phosphite, monododecyl phosphite, di(p-tert-butyl phenyl) phosphite, decyl phenyl phosphite, tert-butyl-phenyl 2-ethylhexyl phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, 2-cyclohexyloxy-5,5-diethyl dioxaphosphorinane, monophenyl phosphite, 2-ethylhexyl phosphite, isooctyl phosphite, cresyl phosphite, t-octylphenyl phosphite, t-butyl phosphite, diphenyl phosphite, diisooctyl phosphate, dicresyl phosphite, dioctylphenyl phosphite, didodecyl phosphite, di-α-naphthyl phosphite, ethylene phosphite, butyl cresyl phosphite, phenyl-mono-2-ethylhexyl phosphite, isooctyl monotolyl phosphite and phenyl cyclohexyl phosphite.

Exemplary pentaerythrityl phosphites are 3,9-diphenoxy-2,4,8,10-tetraoxa-3,9-diphosphaspiro-(5,5)-undecane (diphenyl-pentaerythritol-diphosphite), 3,9-di(decyloxy)-2,4,8,10-tetraoxa-3,9-diphosphaspiro (5,5) undecane, 3,9-di(isodecyloxy) 2,4,8,10-tetraoxa-3,9-diphosphaspiro-(5,5)-undecane, 3,9-di(octadecyloxy)2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)2,4,8,10-tetraoxa-3,9-diphosphaspiro-(5,5)-undecane 3,9-di(lauryl)-2,4,8,10-tetraoxa-3,9-diphosphaspiro-(5,5)-undecane, 3,9-di-p-tolyoxy-2,4,8,10 tetraoxa-3,9-diphosphaspiro-(5,5)-undecane; 3,9-di(methoxyethyl)2,4,8,10-tetraoxa-3,9diphosphaspiro-(5,5)-undecane; 3-methoxyethyl-o-isodecyl-2,4,8,10-tetraoxa-3,9-diphosphaspiro-(5,5)-undecane; 3,9-di(ethoxyethyl)-2,4,8,10-tetraoxa-3,9-diphosphaspiro-(5,5)-undecane; 3,9-di(butoxyethyl)-2,4,8,10-tetraoxa-3,9-diphosphaspiro-(5,5)-undecane; 3-methoxyethyl-9-butoxyethyl-2,4,8,10-tetraoxa-3,9-diphosphaspiro-(5,5)-undecane; 3,9-di(methoxyethoxyethyl)2,4,8,10-tetraoxa-3,9-diphosphaspiro-(5,5)-undecane; 3,9-di(butoxyethoxyethyl-2,4,8,10-tetraoxa-3,9-diphosphaspiro-(5,5)-undecane; 3,9-di(methoxyethoxyethyl)-2,4,8,10-tetraoxa-3,9-diphosphaspiro-(5,5)-undecane; 3,9-di(methoxypolyethoxyethyl)-2,4,8,10-tetraoxa-3,9-diphosphaspiro (5,5) undecane (where the polyethoxyethyl group has an average molecular weight of 350) 3,9-di(methoxypolyethoxyethyl)-2,4,8,10-tetraoxa-3,9-diphosphaspiro (5,5) undecane (where the polyethoxyethyl group has an average molecular weight of 550)

Exemplary of the bis aryl phosphites are: bis(4,4'-thio-bis(2-tertiary butyl-5-methyl-phenol)) isooctyl phosphite, mono(4,4'-thio-bis(2-tertiary-butyl-5-methyl-phenol)) di-phenylphosphite, tri-(4,4'-n-butylidene-bis(2-tertiary-butyl-5-methyl-phenol)) phosphite, (4,4'-benzylidene-bis(2-tertiary-butyl-5-methyl-phenol)) diphenyl phosphite, isooctyl 2,2'-bis(-parahydroxyphenyl) propane phosphite, tri-decyl 4,4'-n-butylidene-bis(-2-tertiary butyl-5-methylphenol)-phosphite, 4,4'-thiobis(2-tertiary butyl-5-methyl-phenol) phosphite, 2-ethylhexyl-2,2'-methylene-bis(4-methyl-6-1'-methylcyclohexyl) phenol phosphite, tri(-2,2'-bis-(para-hydroxyphenyl) propane) phosphite, tri(-4,4'-thio-bis(2-tertiary-butyl-5-methyl-phenol) phosphite, isooctyl-(2,6-bis(2'-hydroxy-3,5-dinonyl-benzyl)-4-nonyl phenyl)) phosphite, tetra-tridecyl 4,4'n-butylidene-bis(2-tertiary butyl-5-methyl phenyl)-diphosphite, tetra-isooctyl 4,4'-thiobus(2-tertiary butyl-5-methyl phenyl) diphosphite, 2,2'-methylene-bis(4-methyl 6-1'-methyl cyclo-hexyl phenyl) poly-phosphite, isooctyl-4,4'-isopropylidene-bis-phenyl polyphosphite, 2-ethylhexyl-2,2'-methylene-bis(4-methyl-6,1'-methyl-cyclohexyl) phenyl triphosphite, tetra-tridecyl-4,4'-oxydiphenyl diphosphite, tetra-n-dodecyl-4,4'-n-butylidenebis (2-tertiary-butyl-5-methylphenyl) diphosphite, tetra-tridecyl-4,4'-isopropylidene bisphenyl diphosphite, hexa-tridecyl butane-1,1,3-tris(2'-methyl-5'-tertiary-butylphenyl-4'-) triphosphite.

The phenol stabilizers contain one or more phenolic hydroxyl groups, and one or more phenolic nuclei and can contain from about eight to about 300 carbon atoms. In addition, the phenolic nucleus can contain any oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about 18 carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure;

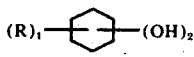

R is selected from the group consisting of hydrogen; halogen: and organic radicals containing from one to about thirty carbon atoms, such as alkyl, aryl, alkenyl, alkaryl, aralkyl, cycloalkenyl, cycloalkyl, alkoxy, and acyl $(R'\overset{\text{O}}{\underset{\|}{C}}-)$, where R' is aryl, alkyl or cycloalkyl.

$x_1$ and $x_2$ are integers from 1 to 4, and the sum of $x_1$ and $x_2$ does not exceed 6.

The polycyclic phenol employed in the stabilizer combination is one having at least two aromatic nuclei linked by a polyvalent linking radical, as defined by the formula:

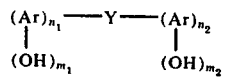

wherein Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to 20 carbon atoms.

Ar is a phenolic nucleus which can be a phenyl or a polycarbocyclic group having condensed or separate phenyl rings: each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from 1 to 5, and $n_1$ and $n_2$ are numbers of 1 or greater, and preferably from 1 to 4.

The aromatic nucleus Ar can, in addition to phenolic hydroxyl groups, include one or more inert substituents. Examples of such inert substituents include hydrogen, halogen atoms, e.g. chlorine, bromine and fluorine; organic radicals containing from one to about 30 carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

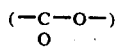

groups. Usually, however, each aromatic nucleus will not have more than about 18 carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluorenyl groups.

When Ar is a benzene nucleus, the polyhydric polycyclic phenol has the structure:

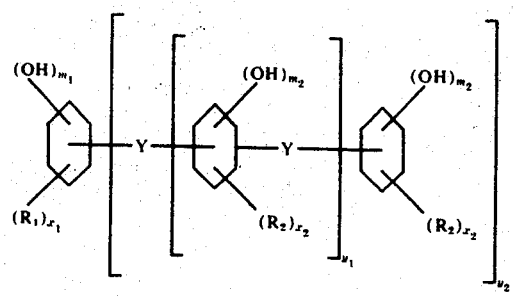

wherein $R_1$, $R_2$ and $R_3$ are inert substituent groups as

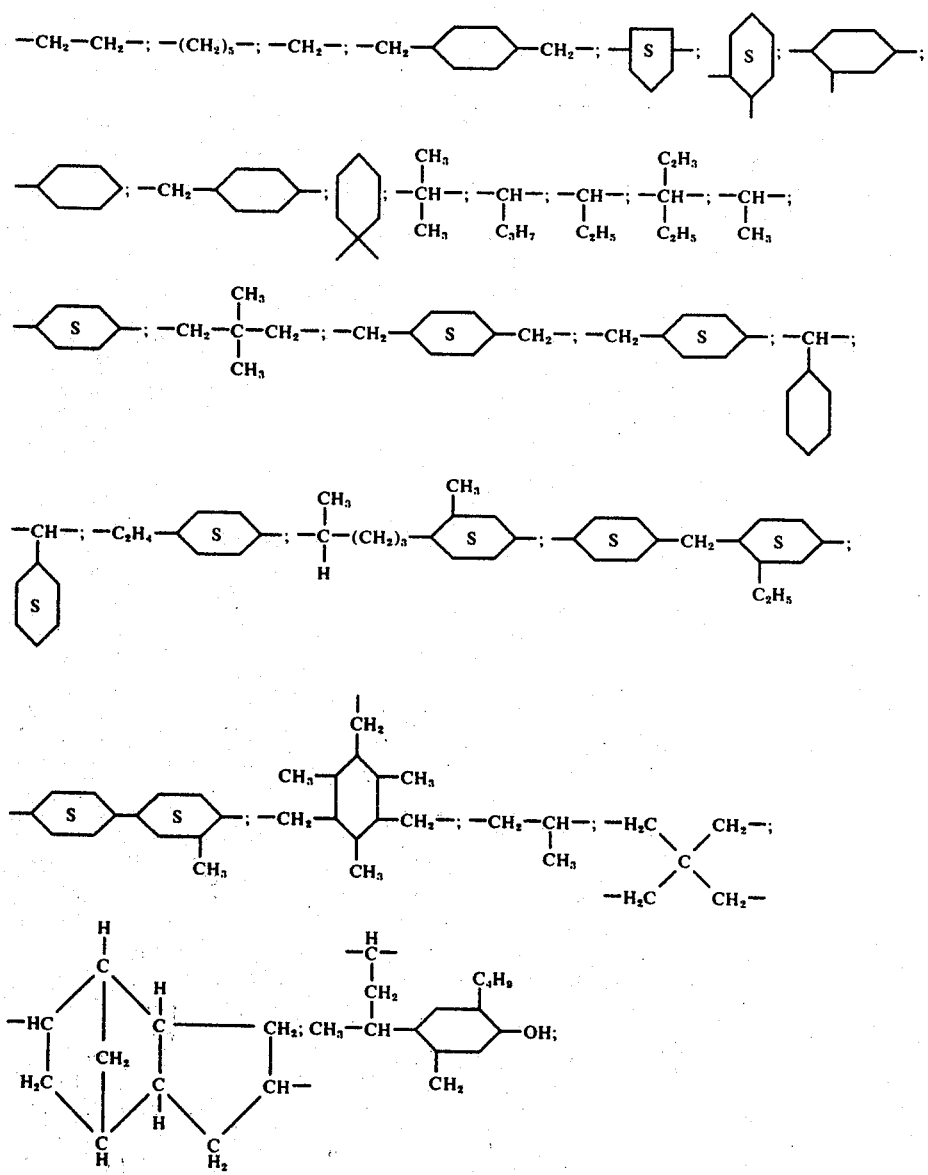

described in the previous paragraph, $m_1$ and $m_2$ are integers from 1 to a maximum of 5, $m_2$ is an integer from 1 to a maximum of 4, $x_1$ and $x_2$ are are integers from 0 to 4, and $x_2$ is an integer from 0 to 3; $y_1$ is an integer from 0 to about 6 and $y_2$ is an integer from 1 to 5, preferably 1 or 2.

Preferably, the hydroxyl groups are located ortho and/or para to Y.

Exemplary Y groups are alkylene, alkylidene, and alkenylene arylene, alkyl arylene, arylalkylene, cycloalkylene, cycloalkylidene, and oxa- and thia-substituted such groups; carbonyl groups, tetrahydrofuranes, esters and triazino groups. The Y groups are usually bi, tri, or tetravalent, connecting two, three or four Ar groups. However, higher valence Y groups, connecting more than four Ar groups, can also be used. According to their constitution, the Y groups can be assigned to subgenera as follows:

1. Y groups where at least one carbon in a chain or cyclic arrangement connect the aromatic groups, such as 2. Y groups where only atoms other than carbon link the aromatic rings, such as

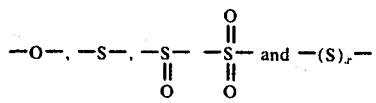

where *x* is a number from 1 to 10;

3. Y groups made up of more than a single atom including both carbon and other atoms linking the aromatic nuclei, such as

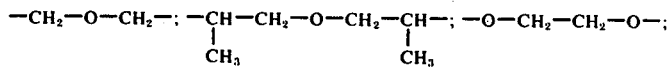

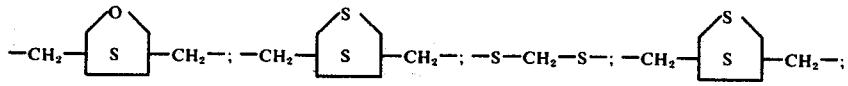

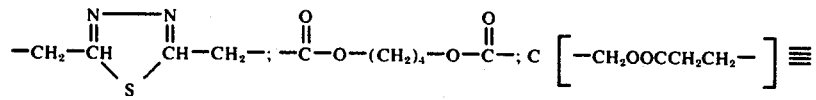

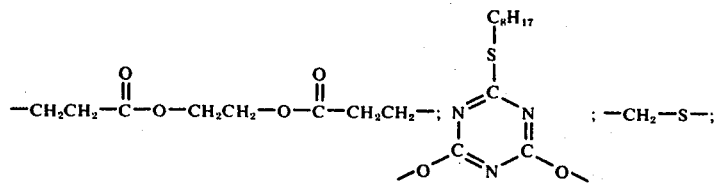

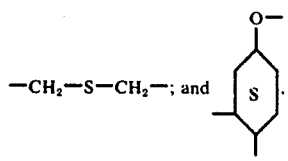

Although the relation of effectiveness to chemical structure is insufficiently understood, many of the most effective phenols have Y groups of subgenus 1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-ditert-butyl-4-methyl phenol, 2-tert-butyl-4-methoxy phenol, 2,4-dinonyl phenol, 2,3,4,5-tetradecyl phenol, tetrahydro-α-naphthol,o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl-phenol, o- and m-tert-butyl-p-hydroxy-anisole, p-n-decyloxyphenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol methyl-p-hydroxybenzoate, p-di-chlorobenzoyl-aminophenol and p-hydroxysalicyl anilide.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxy-benzene, 4-isohexylcatechol, 2,6-ditertiary-butyl-resorcinol, 2,6-diisopropyl-phloroglucinol.

Exemplary polyhydric polycyclic phenols methylene-bis-(2,6-ditertiarybutyl-phenol), 2,2-bis-(4-hydroxy phenyl)-propane, methylene,-bis(p-cresol), 4,4'-benzylidenebis-(2-tertiary butyl-5-methyl-phenol), 4,4 -cyclohexylidenebis-(2-tertiary butylphenol), 2,2'-methylenebis(4-methyl-6-(1'-methyl-cyclohexyl)-phenol), 2,6-bis(2'-hydroxy-3'-tertiary-butyl-5'-methylbenzyl)-4-methylphenol, (2-tertiary-butyl-5-methyl-phenol), 2,2'-bis(4-hydroxy-phenyl) butane, ethylenebis-(p-cresol), 4,4'-oxobis-phenol, 4,4'-oxobis (3-methyl-5-isopropyl-phenol), 4,4'-oxobis-(3-methyl-phenol), 2,2'-oxobis-(4-dodecyl-phenyl), 2,2'-oxobis-(4-methyl-5-tertiary-butyl-phenyl), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6,(1'-methyl-cyclohexyl)-phenol), 4,4'-cyclohexylenebis-(2-tertiary-butyl-phenol), 2,6-bis-(2'-hydroxy-3'-t'-butyl-5'-methyl-benzyl)-4-methyl-phenol, 4,4'-oxobis (naphthalene-1,5-diol), 1,3'-bis(naphthalene-2,5-diol) propane, and 2,2'-butylenebis-(naphthalene-2,7-diol), (3-methyl-5-tert-butyl-4-hydroxyphenyl)-4'-hydroxyphenyl) propane, 2,2'-methylenebis-(4-methyl-5-isopropylphenol), 2,2'-methylenebis-(5-tert-butyl-4-chlorophenol), (3,5-di-tert-butyl-4-hydroxyphenyl)-(4'-hydroxyphenyl)ethane, (2-hydroxy-phenyl)-(3',5'-di-tert-butyl-4'4-hydroxyphenyl)ethane, 2,2'-methylenebis-(4-octylphenol), 4,4'-propylenebis-(2-tert-butyl-phenol), 2,2'-isobutylenebis-(4-nonylphenyl), 2,4-bis-(4-hydroxy-3-t-butylphenoxy)-6-(n-octylthio)-1,3,5-triazine, 2,4,6-tris(4-hydroxy-3-t-butylphenoxy)-1,3,5-triazine, 2.2'-bis-(3-t-butyl-4-hydroxyphenyl) thiazolo-(5,4-d)thiazole, 2,2'-bis-(3-methyl-5-t-butyl-4-hydroxyphenyl) thiazolo-(5,4-d)-thiazole, 4,4'-bis-(4-hydroxy-phenyl)pentanoic acid octadecyl ester, cyclopentylene-4,4'-bisphenol, 2-ethylbutylene-4,4'-bisphenol, 4,4'-cyclooctylenebis(2-cyclohexylphenol), β,β-thiodiethanolbis(3-tert-butyl-4-hydroxyphenoxy acetate), 1,4-butanediobis-(3-tert-butyl-4-hydroxyphenoxy acetate), pentaerythritoltetra(4-hydroxyphenol propionate), 2,4,4'-tri-hydroxy benzophenose, bis-(2-tert-butyl-3-hydroxy-5-methylphenyl) sulfide, bis(2-tert-butyl-4-hydroxy-5-methylphenyl) sulfide, bis(2-tert-butyl-4-hydroxy-5-methyl-phenyl sulfoxide), bis-(3-ethyl-5-tert-butyl-4-hydroxy benzyl) sulfide, bis(2-hydroxy-4-methyl-6-tert-butyl phenyl) sulfide, 4,4'-bis(4-hydroxyphenyl) pentanoic acid octadecyl thiopropionate ester, 1,1,3-tris(2'-methyl-4'-hydroxy-5'-tert-butylphenyl) butane, 1,1,3-tris-(1-methyl-3-hydroxy-4-tert-butylphenyl) butane, 1,8-bis(2-hydroxy-5-methylbenzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)bis-(4-methoxy-6-tert-butyl phenol) and pentaerythritol hydroxyphenyl propionate.

A particularly desirable class of polyhydric polycyclic phenols are the dicyclopentadiene polyphenols, which are of the type:

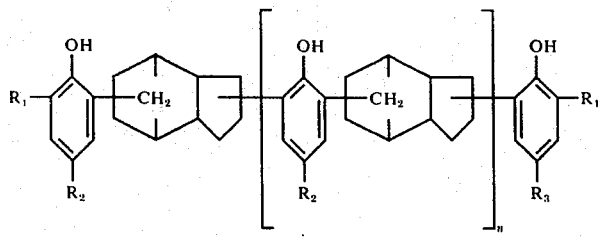

in which $R_1$ and $R_2$ are lower alkyl, and can be the same or different, and $n$ is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri(2-tert-butyl-4-methyl-phenol) of the formula:

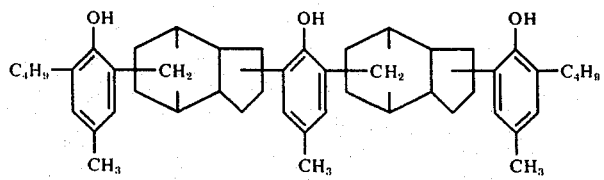

The polyhydric polycyclic phenols used in the invention can also be condensation products of phenol or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see, e.g., U.S. Pat. No. 3,124,555, U.S. Pat. No. 3,242,135, British Pat. No. 961,504.

The thiodipropionic acid ester has the following formula:

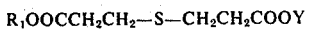

in which $R_1$ is an organic radical selected from the group consisting of hydrocarbon radicals such as alkyl, alkenyl, aryl, cycloalkyl, mixed alkyl aryl, and mixed alkyl cycloalkyl radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of nethiodipropionic acid ester units:

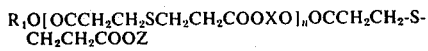

wherein Z is hydrogen, $R_2$ or M; $n$ is the number of thiodipropionic acid ester units in the chain; and X is a bivalent hydrocarbon group of the type of $R_1$; the value of $n$ can range upwards from 1, but there is no upper limit on $n$ except as is governed by the ratio of carbon atoms to sulfur atoms as stated below; and (d) a polyvalent metal M of Group II of the Periodic Table such as zinc, calcium, cadmium, barium, magnesium and strontium.

The molecular weights of the R and Y radicals are taken such that with the remainder of the molecule, the thiodipropionic ester has a total of from about 10 to about 60 carbon atoms per sulfur atom.

Accordingly, the various thiodipropionic acid ester species coming within the above-mentioned categories within the general formula can be defined as follows:
 a. $R_1OOCCH_2CH_2SCH_2CH_2COOH$
 b. $R_1OOCCH_2CH_2SCH_2CH_2COOR_2$
 c. $R_1O[OCCH_2CH_2SCH_2CH_2COOX-O]_nOCCH_2CH_2SCH_2CH_2COOZ$
 d. $[R_1OOCCH_2CH_2SCH_2CH_2COO]_2M$ In the above formulae, $R_1$ and $R_2$, M, X and Z are the same as before. In the polymer (c), as in the other forms of thiodipropionic acid esters, the total number of carbon atoms per sulfur atom is within the range from about 10 to about 60.

The R radical of these esters is important in furnishing compatibility with the polypropylene. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described below.

The aryl, alkyl, alkenyl and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl- and aryl-substituted alkylene radicals such as 1,2-propylene,

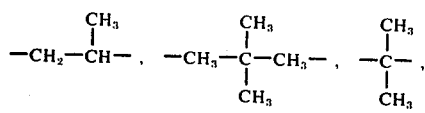

and

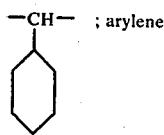; arylene arylene radicals such as phenylene

, methylenephenylene

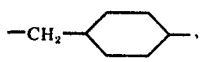, dimethylene phenylene,

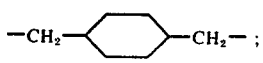;

and alicyclene radicals such as cyclohexylene

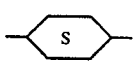

and cyclopentylene

As exemplary of the thiodipropionic acid esters which can be used, there can be mentioned the following: monolauryl thiodipropionic acid, dilauryl thiodipropionate, butyl stearyl thiodipropionate, di(2-ethylhexyl)-thiodipropionate, diisodecyl-thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soybean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl) thiodipropionic acid.

These esters are for the most part known compounds, but where they are not available, they are readily prepared by esterification of thiodipropionic acid and the corresponding alcohol.

When the compound is used in conjunction with a polyvalent metal salt of an organic acid, the organic acid will ordinarily have from about six to about 24 carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic nonnitrogenous monocarboxylic acid having from six to 24 carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is non-aromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reaction, such as by mixing the acid, or anhydride with the corresponding oxide or hydroxide of the metal in a liquid solvent, and heating, if necessary, until salt formation is complete.

The hydrocarbon sulfides and polysulfides can contain one sulfur atom or two or more sulfur atoms linked in a polysulfide unit. Usually, the sulfides and polysulfides will not have more than 50 carbon atoms. They can be defined by the formula:

$$R(S)_n-R$$

wherein $n$ is the number of sulfur atoms and ranges from one to about six, and R is an organic radical having from one to about 30 carbon atoms, such as alkyl, aryl, alkaryl, aralkyl, and cycloalkyl. The following compounds are typical: dibutyl sulfide, didecyl sulfide, diphenyl sulfide, dibenzyl sulfide, butyl octyl sulfide, di-n-dodecyl trisulfide, di-tertiary dodecyl disulfide, di-para-tertiary butyl phenyl trisulfide, dibenzyl disulfide, dibenzyl tetra sulfide, and dibenzyl trisulfide.

Light stabilizers for olefin polymers can also be added, for example, 2-hydroxy benzophenones, o-hydroxyphenyl-benzotriazoles, 1-dioxides of $\alpha,\beta$-benzoisothiazolone and 1,3,5-triazines and nickel organophosphites as disclosed in application Ser. No. 487,614, now U.S. Pat. No. 3,395,112, dated July 30, 1968.

In another embodiment of the invention, as previously indicated, one or more compounds of the invention can be combined with the olefin polymer. Such compositions are readily marketed by the polymer manufacturer as an olefin polymer which can be used in contact with heavy metals, such as copper, and can be combined with the usual olefin polymer stabilizers by the converter in the usual way, without any modification whatsoever, so as to obtain the benefits of the invention due to the presence in the formulation of a compound of the invention. Such compositions have the special advantage that they can be processed using the usual techniques, and, in addition, the usual olefin polymer stabilizer systems will behave virtually in their normal way, even when the composition is in contact with copper.

The preferred stabilizer system of the invention comprises the compounds of the invention and two olefin polymer stabilizers, a phenol, and a thiodipropionic acid ester. An additional fourth ingredient which is included in the preferred systems of the invention but which is not essential is an organic phosphite, and a fifth optional ingredient is a polyvalent metal salt of an organic acid. The olefin polymer stabilizers together give an enhanced stabilization which is not obtainable from any of them alone or in combinations of two with the compound of the invention.

A further improvement in resistance to degradation is obtained if to the stabilizer composition of the invention there be added polyols, such as pentaerythritol and/or dipentaerythritol; or trimethylol propane; oxyacids such as malic acid, tartaric acid or citric acid; epoxy compounds, such as butylepoxy stearate or borate esters, such as phenyl lauryl borate, tristearyl borate and 2,6-di-t-butyl-4-methyl-phenyl borate. Only a small amount is sufficient to give a noticeable improvement. From 0.5 to 10% is satisfactory.

The compounds of the invention are not olefin polymer stabilizers. However, where the compounds of the invention are employed in conjunction with an olefin polymer stabilizer, such as a phenol, and a thiodipropionic acid ester, and the olefin polymer is in contact with copper, the polymer's resistance to embrittlement and reduction in melt viscosity at elevated temperatures can be almost as high as though the copper were not present. An organic phosphite and/or a polyvalent metal salt, employed in conjunction with the phenol and thiodipropionic acid ester and compounds of the invention, can further enhance resistance of the polymer to discoloration in the presence of copper. In many cases, an enhanced synergistic stabilizer activity is observed in such combinations.

The compound of the invention can minimize any catalytic effect of heavy metals such as copper, lead, cobalt, and chromium, on the rate of degradation of the olefin polymer in the presence of olefin polymer stabilizers. Very small amounts can significantly reduce this effect. Amounts within the range from about 0.001 to about 5% by weight of the polypropylene are satisfactory. Preferably, from 0.05 to 1% is employed.

The amount of total stabilizer including the olefin polymer stabilizer and the compound of the invention is within the range from about 0.0001 to about 7.5%, preferably from 0.01 to 5%. Of this, the olefin polymer stabilizer comprises from about 0.001 to about 5% by weight, and the compound of the invention from about 0.0001 to about 5% by weight. The preferred olefin polymer stabilizer comprises from about 0.025 to about 1% of a phenol, from about 0.05 to about 1% of a thiodipropionic acid ester, and optionally, from about 0.05 to about 1.25% of a phosphite, and from about 0.025 to about 0.75% of a polyvalent metal salt, when present.

The compounds of the invention and the olefin polymer stabilizers may be formulated as a simple mixture for incorporation in the polymer by the polymer manufacturer or by the converter. An inert organic solvent can be used to facilitate handling, if the ingredients do not form a homogeneous mixture or solution.

Polypropylene solid polymer can be defined in a manner to differentiate it from other polyolefins as having a density within the range of from 0.86 to 0.91, and a melting point above 150° C. The stabilizer of the invention is applicable to all such polypropylenes, as distinguished from polypropylenes in the liquid form or in semiliquid or gel-like forms, such as are used as greases and waxes.

The stabilizer system of the invention is applicable to polypropylenes prepared by any of the various procedures, for the molecular weight and tacticity are not factors affecting this stabilizer. Isotactic polypropylene, available commercially under the trade name Profax, Escon and Olefane and having a softening or hot-working temperature of about 350° F. is an example of a sterically regular polypropylene polymer.

Mixtures of polypropylene with other compatible polymers and copolymers of propylene with copolymerizable monomers also can be improved in accordance with this invention. For example, mixtures of polyethylene and polypropylene, and copolymers of propylene and ethylene which contain a sufficient amount of propylene to present the instability problem that is resolved by the compounds of the invention, may be improved by the addition of one or more of the compounds of the invention, alone or in combination with other polypropylene stabilizers.

The stabilizer systems of the invention may also be used with polyolefins higher than polypropylene, such as polybutylene and polyisobutylene.

The compounds of the invention and stabilizer systems including the same are incorporated in the polymer in suitable mixing equipment, such as a mill or a Banbury mixer. If the polypropylene has a melt viscosity which is too high for the desired use, the polypropylene can be worked until its melt viscosity has been reduced to the desired range before addition of the stabilizer. However, polypropylenes in a range of workable melt viscosities are now available. Mixing is continued until the mixture is substantially uniform. The resulting composition is then removed from the mixing equipment and brought to the size and shape desired for marketing or use.

The stabilized polypropylene can be worked into the desired shape, such as by milling calendering, extrusion or injection molding or fiber-forming. In such operations, it will be found to have a considerbly improved resistance to reduction in melt viscosity during the heating, as well as a better resistance to discoloration and embrittlement on ageing and heating.

The following Examples represent preferred embodiments of the stabilizer compositions and olefin polymer compositions of the invention.

EXAMPLES 1 TO 31

Polypropylene compositions were prepared, stabilized by combinations of compounds of the invention and known polypropylene stabilizers, and were evaluated for their resistance to oxidative degradation in the presence of copper. An accelerated oxidation test was employed, to determine the effective useful life of the polypropylene.

The base olefin polymer composition tested was as follows:

|  | Parts by Weight |
|---|---|
| Polypropylene (Profax 6501) | 100 |
| 1,1,3-tris(2'-methyl-4'-hydroxy-5'-tert-butylphenyl) butane | 0.07 |
| Distearyl thiodipropionate | 0.30 |
| Trinonylphenyl phosphite | 0.13 |
| 3-Amido-1,2,4-triazole of the invention as listed in Table I | 0.30 |

The components forming the above formulation were milled for 10 minutes on a mixing roll, and the resulting composition was extruded at 250° C. through a 30 mm extruder at 30 rpm. Sheets of 0.5 thickness was obtained by compression-molding at 180° C. under a pressure of 200 kg/cm$^2$ for 5 minutes.

A sandwich was prepared composed of rolled copper sheet-polypropylene sheet-rolled copper sheet. The polypropylene used was 40 × 50 mm and the rolled copper sheet used was 0.03 mm thick. The sandwich was pressed flat with a 145 g. force, and the degradation of the copper sheet evaluated by heating the sandwich at 152° C. in a hot pack oven at atmospheric pressure in air.

As the Control, the base composition was tested, without the amidotriazole.

Table I below sets out the results of the test for each compound tested.

TABLE I

| Example No. | Compound | Oven Test at 152° C. Hrs. to Failure | Color |
|---|---|---|---|
| Control | None | 20 | None |
| 1 | (cyclohexyl-OH)-CONH-C(=N)-N(H)-CH=N (triazole) | 584 | None |
| 2 | Cl-(cyclohexyl-OH)-CONH-C(=N)-N(H)-CH=N (triazole) | 540 | None |
| 3 | (cyclohexyl-OH, Cl)-CONH-C(=N)-N(H)-CH=N (triazole) | 502 | None |

TABLE I-continued

| Example No. | Compound | Oven Test at 152° C. Hrs. to Failure | Color |
|---|---|---|---|
| 4 | 2,4-dihydroxycyclohexanecarboxamide of 3-amino-1,2,4-triazole | 610 | None |
| 5 | 2-hydroxy-5-butoxybenzamide of 3-amino-1,2,4-triazole | 480 | None |
| 6 | 2-hydroxy-5-methylbenzamide of 3-amino-1,2,4-triazole | 600 | None |
| 7 | 2,4-dihydroxybenzamide of 3-amino-1,2,4-triazole | 515 | None |
| 8 | 2-hydroxybenzamide of 3-amino-5-octyl-1,2,4-triazole ($C_8H_{17}$) | 502 | None |
| 9 | 2-hydroxybenzamide of 3-amino-5-(ethoxyethyl)-1,2,4-triazole ($C_2H_4OC_2H_5$) | 515 | None |
| 10 | 2-hydroxybenzamide of 3-amino-5-(2-pyridyl)-1,2,4-triazole | 540 | None |
| 11 | 2-hydroxythiobenzamide of 3-amino-5-phenyl-1,2,4-triazole | 492 | None |
| 12 | 2-hydroxythiobenzamide of 3-amino-5-methyl-1,2,4-triazole ($CH_3$) | 509 | None |

TABLE I-continued

| Example No. | Compound | Oven Test at 152° C. Hrs. to Failure | Color |
|---|---|---|---|
| 13 | 2-hydroxynaphthalene-3-carboxamide linked to 3-amino-1H-1,2,4-triazole | 482 | None |
| 14 | 1-hydroxynaphthalene-2-carboxamide linked to 3-methyl-1H-1,2,4-triazol-5-yl | 444 | None |
| 15 | salicylamide linked to 3-(2-phenylthiomethyl)-1H-1,2,4-triazol-5-yl | 480 | None |
| 16 | bis-salicylamide linked via 3,3'-bi-1H-1,2,4-triazole | 540 | None |
| 17 | bis-salicylamide linked via 3,3'-ethylene-bis(1H-1,2,4-triazole) | 437 | None |
| 18 | bis(5-octylsalicylamide) linked via 3,3'-tetramethylene-bis(1H-1,2,4-triazole) | 516 | None |
| 19 | bis(3-hydroxy-2-naphthamide) linked via 3,3'-(ethene-1,2-diyl)-bis(1H-1,2,4-triazole) | 429 | None |
| 20 | bis-salicylamide linked via 3,3'-(1,2-dihydroxyethylene)-bis(1H-1,2,4-triazole) | 380 | None |
| 21 | bis(2-hydroxy-5-octyloxybenzamide) linked via 3,3'-(1,4-phenylene)-bis(1H-1,2,4-triazole) | 553 | None |

TABLE I-continued

| Example No. | Compound | Oven Test at 152° C. Hrs. to Failure | Color |
|---|---|---|---|
| 22 | (structure with two triazole-C₂H₅ groups linked via -NHCO-phenol-CH₂-phenol-CONH-) | 506 | None |
| 23 | (structure with two triazole-C₈H₁₇ groups linked via -NHCO-phenol-CH₂-S-CH₂-phenol-CONH-) | 532 | None |
| 24 | (structure with two triazole-CH groups linked via -NHCO-phenol-CH(C₃H₇)-phenol-CONH-) | 516 | None |
| 25 | (structure with two triazole-CH groups linked via -NHCO-phenol-CH₂-SO₂-CH₂-phenol-CONH-) | 452 | None |
| 26 | (structure with two triazole-CH₃ groups linked via -NHCO-phenol-CH₂-SS-CH₂-phenol-CONH-) | 320 | None |
| 27 | (structure with two triazole-C₃H₇ groups linked via -NHCO-phenol-NHCSNH-phenol-CONH-) | 481 | None |
| 28 | (triazole-NHCO-phenyl-SC₂H₄COOCH₃) | 301 | None |
| 29 | (2-hydroxycyclohexyl-CONH-triazole-CH₃) | 590 | None |
| 30 | (2-hydroxycyclohexyl-CONH-triazole-CH₂O-cyclohexyl) | 407 | None |

TABLE I-continued

| Example No. | Compound | Oven Test at 152° C. Hrs. to Failure | Color |
|---|---|---|---|
| 31 | 2-mercaptocyclohexyl-CONH-C(=N)-NH-N=C-C₂H₅ (triazole ring with HS substituent) | 521 | None |
| 32 | 3-hydroxy-2-naphthoyl-CONH-C(=N)-NH-N=C-CH₃ (triazole) | 444 | None |

EXAMPLE 32

In order to see the effects of the amidotriazoles on improving the resistance to degradation of polypropylene in the presence of copper powder, sample sheets were prepared of the following formulation:

| | Parts by Weight |
|---|---|
| Polypropylene (Profax 6501) | 100 |
| 1,1,3-tris(2'-methyl-4'-hydroxy-5'-tert-butylphenyl)butane (Topanol CA) | 0.07 |
| Distearyl thiodipropionate | 0.30 |
| Trinonylphenyl phosphite | 0.13 |
| 2-Amido,1,2,4-triazole | 0.30 |
| Copper Powder | 1.50 |

The formulation was blended on a mill at 185° C. for 5 minutes. Then polypropylene sheets 0.4 thick were made by compression-molding at 180° C. under a pressure of 200 kg/cm² for 5 minutes. The sheets were cut 10 × 20 mm and heated in a circulating air oven at 160° C. until failure.

TABLE II

| Example No. | Compound | Oven Test at 160° C. Hrs. to Failure |
|---|---|---|
| Control 32 | None | 12 |
| | 5-ethyl-3-salicyloylamido-1,2,4-triazole | 234 |

(structure: 2-hydroxyphenyl-CONH-C(=N)-NH-N=C-C₂H₅)

The stabilizing effect of the amidotriazole is apparent from the data.

EXAMPLE 33

In order to see the effect of the amidotriazole against heavy metal in polymerization catalyst, saple polypropylene films were prepared of the following formulation:

| | Parts by Weight |
|---|---|
| Polypropylene (Profax 6501) | 100 |
| Distearyl thiodipropionate | 0.25 |
| Amidotriazole | 0.10 |

The time required for the film to absorb 10 cc. of oxygen per gram of sample when heated at 160° C. was determined, and is listed in the following Table III.

TABLE III

| Example No. | Compound | Oven Test at 160° C. Hrs. to Failure |
|---|---|---|
| Control | None | 30 min. |
| 33 | 3(5-methylsalicyloyl)amido-1,2,4-triazole | 200 hrs. |

(structure: 2-hydroxyphenyl-CONH-C(=N)-NH-N=C-CH₃)

The stabilizing effect of the amidotriazole is evident from the above data.

EXAMPLES 34 TO 37

In order to see the effect of the amidotriazole in enhancing the resistance to degradation of polypropylene in the presence of heavy metal pigments, sample films were prepared of the following formulation:

| | Parts by Weight |
|---|---|
| Polypropylene (Profax 6501) | 100 |
| 1,1,3-tris(2'-methyl-4'-hydroxy-5'-tert-butylphenyl)butane (Topanol CA) | 0.07 |
| Distearyl thiodipropionate | 0.30 |
| Trinonylphenylphosphite | 0.17 |
| Cu phthalocyanine blue | 0.50 |
| Amidotriazole | 0.30 |

The hours to failure were measured at 160° C. Test results are listed in Table IV:

TABLE IV

| Example No. | Compound | Oven Test at 160° C. Hrs. to Failure |
|---|---|---|
| Control | None | 210 |
| 34 | HO-C₆H₃(C₈H₁₇)-CONH-C(=N-NH-N=)-C(C₄H₉)=C-(=N-NH-N=)C-NHCO-C₆H₃(OH)(C₈H₁₇) | 381 |
| 35 | HO-C₆H₃(Cl)-CONH-C(=N-NH-N=)CH | 359 |
| 36 | (2-hydroxynaphthyl)-CONH-C(=N-NH-N=)CH | 391 |
| 37 | HO-C₆H₃(Cl)-CONH-C(=N-NH-N=)C-CH₃ | 362 |

The effectiveness of the amidotriazole under these conditions is quite remarkable.

The amidotriazoles of the invention are also effective antioxidants in any hydrocarbon having a long or short carbon chain. Thus, hydrocarbon fuels, such as gasoline, kerosene, jet fuel, and fuel oil, have an increased resistance to oxidative deterioration when a compound of the invention is incorporated therein.

Hydrocarbon fuels containing organometallic additives, such as tetraethyl lead and tetramethyl lead, also have increased oxidative stability. Lubricating oils and functional fluids derived from naturally-occurring hydrocarbons as well as synthetic lubricating oils and functional fluids also have their resistance to oxidation increased by the antioxidants of the invention.

The following Example is illustrative:

EXAMPLE 38

A kerosene composition was prepared to the following formulation:

| | Parts by Weight |
|---|---|
| Kerosene | 100 |
| Cu stearate | 0.02 |
| 2,5-di-tert-butyl-p-cresol | 0.01 |
| 3-salicyloylamido-1,2,4-triazole | 0.01 |

The composition was stored at 40° C. for 40 days, then carbonyl absorption (as a measure of oxidation to C—O) was measured with an infrared spectrometer. The composition containing 3-salicyloylamido-1,2,4-triazole (Example 38) showed no carbonyl absorption, but the control composition without amidotriazole showed a remarkable increase in carbonyl content.

The amidotriazoles of the invention are also useful stabilizers for acrylonitrile-butadiene-styrene polymers, as a class. Many of the ABS polymers available commercially are prepared by dispersing an elastomeric phase such as a diene homopolymer such as polybutadiene into a rigid styrene-acrylonitrile copolymer or a terpolymer. The elastomeric phase can also be a copolymer with styrene or acrylonitrile, or a styrene acrylonitrile graft on an elastomeric substrate, such as polybutadiene. The contribution of each of the acrylonitrile, styrene and butadiene is important. Terpolymers of the three monomers do not always have the desired properties, and ABS graft copolymers are most common, and include a styrene-acrylonitrile copolymer phase and a preformed polybutadiene substrate on which is grafted styrene and acrylonitrile, usually by emulsion, bulk or suspension polymerization. See Chemistry and Industry, Aug. 13, 1966, pp. 1399–1405. All of these are encompassed herein under the terms "acrylonitrile-butadiene-styrene polymer," or "ABS polymer."

ABS polymers generally contain from about 15 to about 35% acrylonitrile, from about 5 to about 35% butadiene, and from about 40 to 80% styrene, by weight. The matrix usually has a molecular weight of from about 200,000 to about 450,000 or more, and a density of from about 0.99 to about 1.09.

The acrylonitrile portion of the ABS polymer imparts chemical resistance to the polymer; the styrene portion of the ABS polymer imparts good fabrication characteristics to the polymer; and the rubber or butadiene portion of the ABS polymer provides rubberiness and toughness to the polymer. Accordingly, chemical resistance, good fabrication characteristics, and rubberiness and toughness features can be varied in any given ABS polymer by varying the quantities of the acrylonitrile, butadiene and styrene. For example, the impact strength of the ABS polymer can be increased by increasing the amount of butadiene in the polymer. However, increase in impact strength is accompanied by slight reduction in heat resistance, rigidity, electrical properties and some of the other strength properties.

Heat resistance of the ABS polymer can be improved by increasing the amount of acrylonitrile in the polymer. However, increased heat resistance, such as high heat-distortion temperature, usually is accompanied by decreased impact strength, especially at low temperatures.

The amidotriazoles of the invention are effective in improving heat resistance of ABS polymer without deleterious effect on other physical properties. These compounds improve ABS polymer prepared by polymerizing acrylonitrile monomer and styrene monomer in a previously prepared polybutadiene latex, or butadiene copolymer rubber latex, under such conditions that an appreciable portion of the acrylonitrile and styrene become grafted or polymerized directly on the polybutadiene molecules, as in U.S. Pat. No. 2,439,202, dated Apr. 6, 1948, to Daly, and U.S. Pat. No. 2,600,024, dated June 10, 1952, to Romeyn et al., and with ABS graft copolymer blends of all types such as blends with styrene-acrylonitrile resin, or nitrile copolymer rubber, as in U.S. Pat. No. 2,802,808, dated Aug. 13, 1957, to Hayes.

ABS polymers are conventionally blended with additives such as fillers, pigments and lubricants. Appropriate pigments and fillers are, for example, flour, cotton, shredded or chopped cloth, talc, chopped canvas, paper pulp fibers, asbestos, powdered mica, calcium carbonate, carbon, graphite, quartz, diatomaceous earth, silica, fibrous glass, barytes, calcium silicate, iron, barium sulfate, litharge, clay and titanium dioxide. Fillers are normally used in an amount of from about 2 to about 40% by weight of the polymer. Typical lubricants are mineral oil, natural and synthetic waxes, fatty acids such as stearic acid, alkaline earth and heavy metal stearates, and aliphatic alcohols, ketones, and epoxides having from about 16 to about 60 carbon atoms in the molecule, including stearyl alcohol, palmitone, behenone, oleone, cetyl palmitate, 1,2-epoxydocosane, and isooctyl epoxy-stearate, in amounts of from about 0.2 to 3% of the polymer.

A sufficient amount of the compound of the invention is used to enhance the resistance of the ABS polymer against discoloration upon exposure to elevated temperatures. Small amounts are usually adequate. Amounts within the range from about 0.0001 to about 5% by weight of the ABS polymer are satisfactory. Preferably, from about 0.05% to about 2% is employed for optimum stabilization.

The stabilizer composition can be formed by simply mixing the individual ingredients in the dry state or in a suitable liquid medium. It is frequently helpful to combine the compound with solvent and water. Another helpful expedient is to prepare the stabilizer composition in the form of an aqueous emulsion. Such an emulsion can be added to a freshly made ABS polymer latex before the polymer is isolated from the latex by the usual procedures of coagulation or spray-drying. A "masterbatch" technique can be utilized to provide both wet and dry combinations of the stabilizer composition with the ABS polymer in proportions for compounding into larger quantities of polymer to be stabilized.

In addition to the amidotriazoles of the instant invention, other heat stabilizers and light stabilizers for ABS polymers can be incorporated, such as, the polyphosphates and polyhydric polycyclic phenols disclosed in U.S. Pat. No. 3,472,813, patented Oct. 14, 1969, to Hecker and Abramoff.

The stabilizer is incorporated in the ABS polymer in suitable mixing equipment, such as a mill, a Banbury mixer, an extruder, and the like.

The stabilized ABS polymer can be worked into the desired shape at elevated temperature by milling, calendering, extrusion or injection molding, or fiber molding.

The following Examples in the opinion of the inventors represent preferred embodiments of ABS polymer compositions of this invention.

EXAMPLE 39

A series of acrylonitrile-butadiene-styrene polymer compositions was prepared having the following formulation:

| | Parts by Weight |
|---|---|
| ABS resin (Blendex 111) | 100 |
| Zn stearate | 0.5 |
| TiO$_2$ | 5.0 |
| Amidotriazole of the invention | 0.5 |

The components forming the above formulation were milled for 10 minutes on a mixing roll, and the resulting composition was extruded at 250° C. through a 30 mm extruder at 30 rpm. Sheets of 0.5 mm thickness were obtained by compression-molding at 180° C. under a pressure of 200 kg/cm² for 5 minutes.

A sandwich was prepared composed of rolled copper sheet-polypropylene sheet-rolled copper sheet. The polypropylene used as 40 × 50 mm and the rolled copper sheet used was 0.03 mm thick. The sandwich was pressed flat with a 145 g. force, and the degradation of the copper sheet evaluated by heating the sandwich at 180° C. in a hot pack oven at atmospheric pressure in air. The test pieces were taken out, and evaluated according to amount of color. The results were as shown in Table V.

TABLE V

| Example No. | Compound | Color |
|---|---|---|
| Control | None | Very strong color |
| 39 | 3'-salicyloylamido 1,2,4-triazole | Slight color |

The stabilizing effect of the amidotriazole is quite marked.

Having regard to the foregoing disclosure, the following is claimed as the inventive and patentable embodiments thereof:

1. 3-Amido-1,2,4-triazoles having the formula:

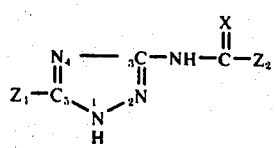

wherein:
a. $Z_1$ is selected from the group consisting of hydrogen, alkyl having from one to 18 carbon atoms; alkylenealkoxy and alkylenearyloxy having from two to 18 carbon atoms; phenyl; pyridyl;

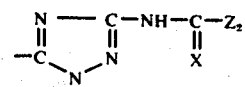

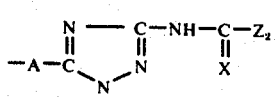

in which A is alkylene having from one to eight carbon atoms or vinylene;
b. X is selected from the group consisting of oxygen and sulfur;
c. $Z_2$ is a benzene or naphthalene ring substituted by from one to two $R_1$ groups and from zero to two $R_2$ groups;
  i. $R_1$ is selected from the group consisting of OH, SH and $SC_2H_4COOCH_3$; and
  ii. $R_2$ is selected from the group consisting of alkyl, alkyl phenyl, alkoxy and alkyl phenoxy, each having from one to 18 carbon atoms; phenyl, phenoxy and halogen; and

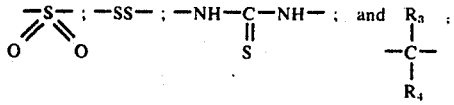

where Y is selected from the group consisting of oxygen; sulfur;

$-S-$; $-SS-$; $-\underset{\underset{O}{\nearrow}\underset{O}{\nwarrow}}{S}-$; $-NH-\underset{\underset{S}{\|}}{C}-NH-$; and $-\underset{\underset{R_4}{|}}{\overset{\overset{R_3}{|}}{C}}-$;

$R_3$ and $R_4$ are selected from the group consisting of hydrogen and alkyl having from one to three carbon atoms, provided, that there are at most two 1,2,4-triazole groups in the molecule.

2. 3-Amido-1,2,4-triazoles in accordance with claim 1, having the formula:

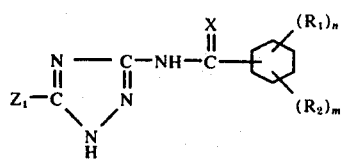

where $n$ is 1 or 2 and $m$ is 0, 1 or 2.

3. 3-Amido-1,2,4-triazoles in accordance with claim 1, having the formula:

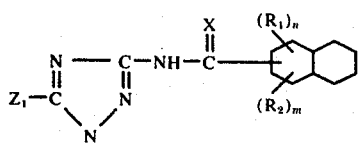

where $n$ is 1 or 2 and $m$ is 0, 1 or 2.
4. 3-Salicyloylamido-1,2,4-triazole.
5. 3-Benzosalicyloylamido-1,2,4-triazole.
6. 3-(5-hydroxy salicyloylamido)-1,2,4-triazole.

* * * * *

UNITED STATES PATENT OFFICE
CERTIFICATE OF CORRECTION

Patent No. 3,997,551          Dated December 14, 1976

Inventor(s) Motonobu Minagawa et al

It is certified that error appears in the above-identified patent and that said Letters Patent are hereby corrected as shown below:

| | | |
|---|---|---|
| Column 1, line 36 | : | "600" should be -- 609 -- |
| Column 3, line 23 | : | "961,931" should be -- 951,931 -- |
| line 46 | : | "130°" should be -- 150° -- |
| line 51 | : | "984,116" should be -- 994,116 -- |
| line 60 | : | "aove" should be -- above -- |
| line 64 | : | "951,933" should be -- 951,936 -- |
| Column 6, line 7 | : | "SR" should be -- $SR_5$ -- |
| line 7 | : | "$R_2$" should be -- $R_5$ -- |
| line 7 | : | delete "the" second occurrence |
| Column 13 | : | Formulae should be corrected as attached starting with second formula: All formulae below are incorrect: |

" 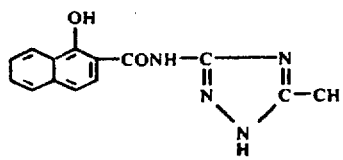          315-330 C.

" 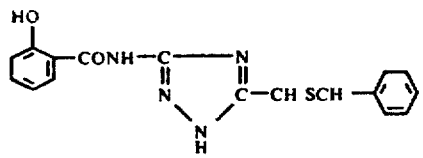          300 C.

UNITED STATES PATENT OFFICE
CERTIFICATE OF CORRECTION

Patent No. 3,997,551   Dated December 14, 1976

Inventor(s) Motonobu Minagawa et al

It is certified that error appears in the above-identified patent and that said Letters Patent are hereby corrected as shown below:

Column 13 (continued)

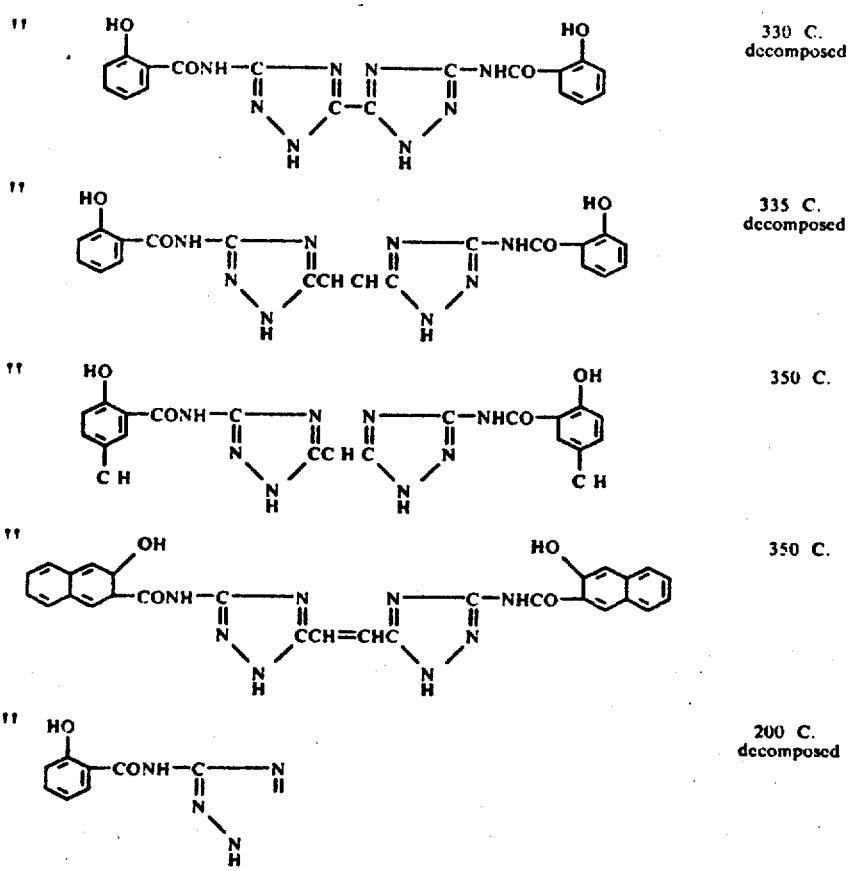

The following formulae should be corrected as follows:

UNITED STATES PATENT OFFICE
CERTIFICATE OF CORRECTION

Patent No. 3,997,551    Dated December 14, 1976

Inventor(s) Motonobu Minagawa et al

It is certified that error appears in the above-identified patent and that said Letters Patent are hereby corrected as shown below:

Column 13 (continued)

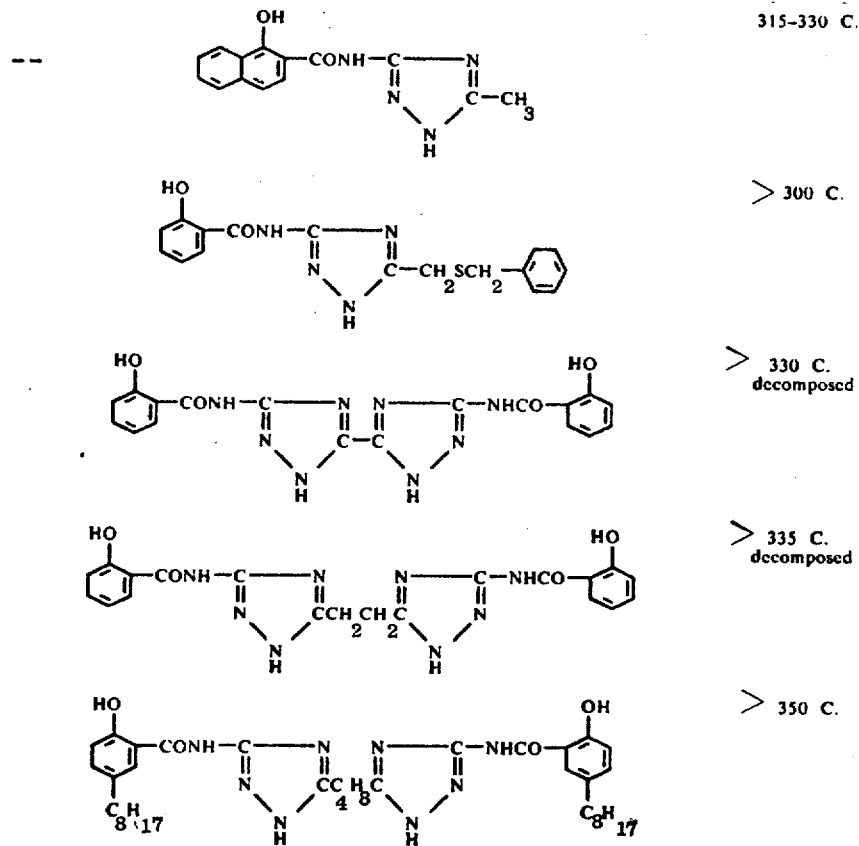

315–330 C.

\> 300 C.

\> 330 C. decomposed

\> 335 C. decomposed

\> 350 C.

UNITED STATES PATENT OFFICE
CERTIFICATE OF CORRECTION

Patent No. 3,997,551      Dated December 14, 1976

Inventor(s) Motonobu Minagawa et al

It is certified that error appears in the above-identified patent and that said Letters Patent are hereby corrected as shown below:

Column 13 (continued)

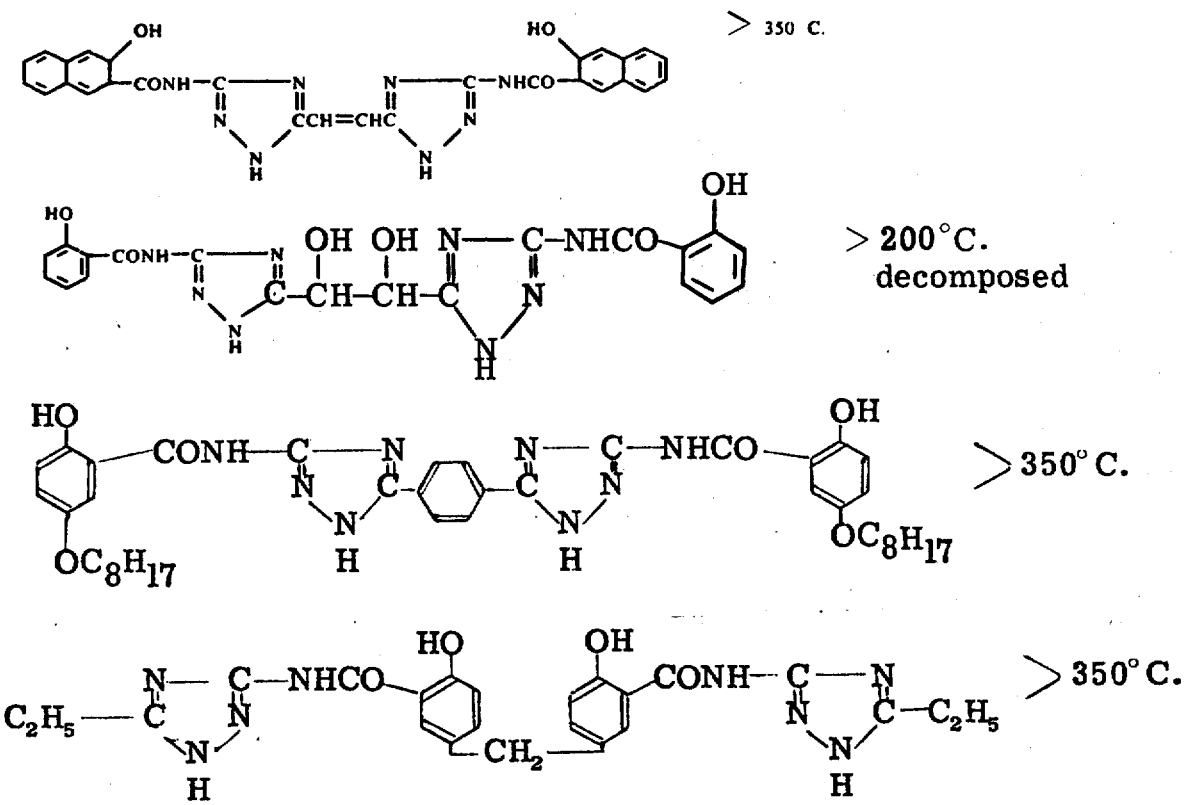

UNITED STATES PATENT OFFICE
CERTIFICATE OF CORRECTION

Patent No. 3,997,551          Dated December 14, 1976

Inventor(s) Motonobu Minagawa et al

It is certified that error appears in the above-identified patent and that said Letters Patent are hereby corrected as shown below:

Column 15, last formula: "
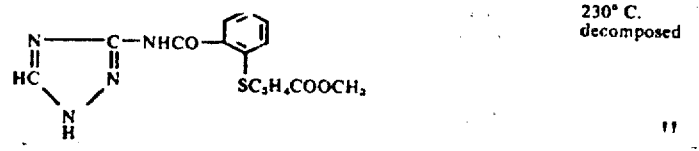
230° C. decomposed
"

should be

--
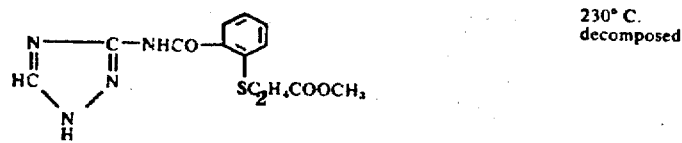
230° C. decomposed
--

Column 17, line 41 : "
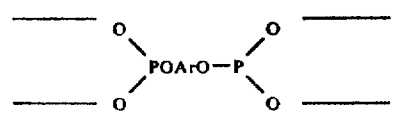
or
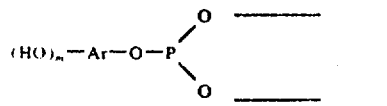
"

should be

--
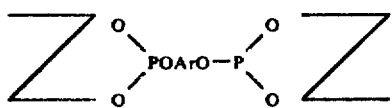
or
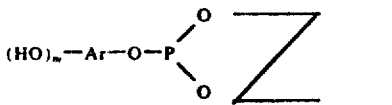
--

UNITED STATES PATENT OFFICE
CERTIFICATE OF CORRECTION

Patent No. 3,997,551         Dated December 14, 1976

Inventor(s) Motonobu Minagawa et al

It is certified that error appears in the above-identified patent and that said Letters Patent are hereby corrected as shown below:

Column 17, line 59 : "by-cyclic" should be --bicyclic--

Column 19, line 60 : "$(R)_1\text{—}\bigcirc\text{—}(OH)_2$" should be --$(R)_{x_1}\text{—}\bigcirc\text{—}(OH)_{x_2}$--

Column 20, line 45 : "(R'C–O)" should be -- $(R'\overset{\parallel}{\underset{O}{C}}\text{–}O)$ -- line 55 : "(–C–O)" should be -- $(\text{–}\overset{\parallel}{\underset{O}{C}}\text{–}O)$ --

Column 21, lines 1-15 : "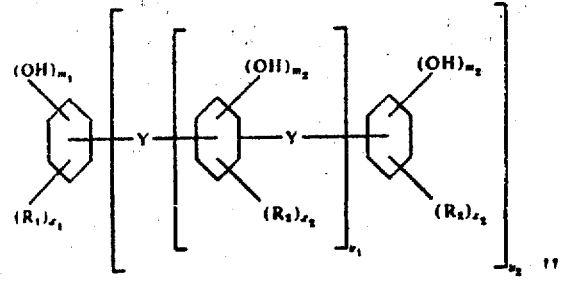"

should be

UNITED STATES PATENT OFFICE
CERTIFICATE OF CORRECTION

Patent No. 3,997,551  Dated December 14, 1976

Inventor(s) Motonobu Minagawa et al

It is certified that error appears in the above-identified patent and that said Letters Patent are hereby corrected as shown below:

Column 21, lines 1-15 (continued) :

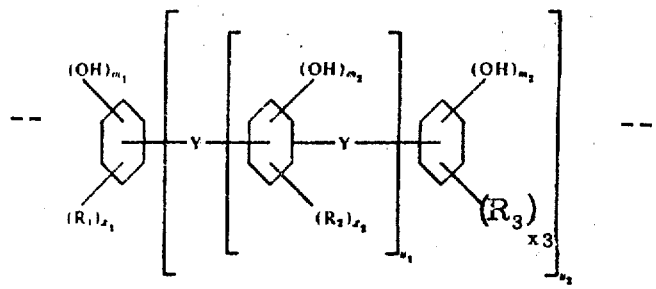

Column 22, last formula :

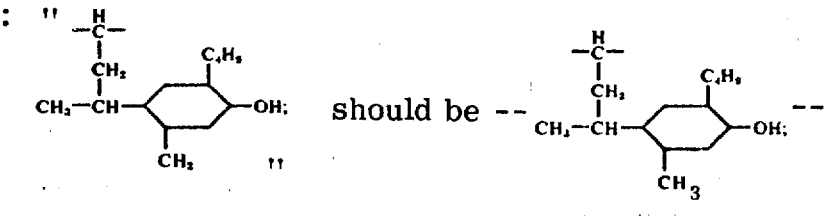

Column 21, line 65 : "$x_2$" should be --$x_3$-- line 65 : delete "are" second occurrence

Column 24, line 4 : "4,4" should be --4,4'--

Column 25, line 2 : "benzophenose" should be --benzophenone--

UNITED STATES PATENT OFFICE
CERTIFICATE OF CORRECTION

Patent No. 3,997,551   Dated December 14, 1976

Inventor(s) Motonobu Minagawa et al

It is certified that error appears in the above-identified patent and that said Letters Patent are hereby corrected as shown below:

Column 25, first formula : "

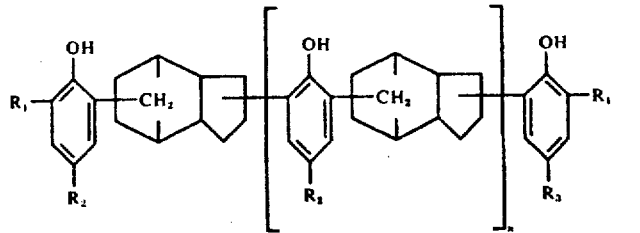

"

should be

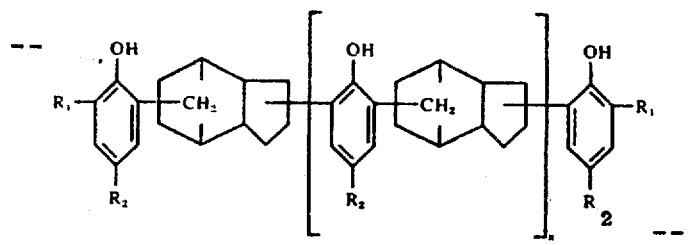

Column 26, line 13 : "nethiodipropionic" should be

-- n thiodipropionic -- line 15 : " $R_1O[OCCH_2CH_2SCH_2CH_2COOXO]_nOCCH_2CH_2S\text{-}CH_2CH_2COOZ$ "

should be

-- $R_1O[OCCH_2CH_2SCH_2CH_2COOXO]_nOCCH_2CH_2\text{-}S\text{-}CH_2CH_2COOZ$ --

UNITED STATES PATENT OFFICE
CERTIFICATE OF CORRECTION

Patent No. 3,997,551   Dated December 14, 1976

Inventor(s) Motonobu Minagawa et al

It is certified that error appears in the above-identified patent and that said Letters Patent are hereby corrected as shown below:

Column 27, line 30 :

line 37 : delete "arylene"

Column 31, line 29 : add a comma (,) after "milling"

line 31 : "considerbly" should be -- considerably --

Column 32, line 27 : "0.5" should be -- 0.5 mm --

Column 33, Example 6 : 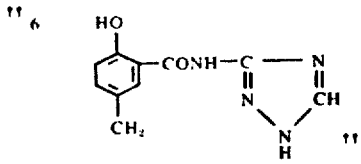

should be

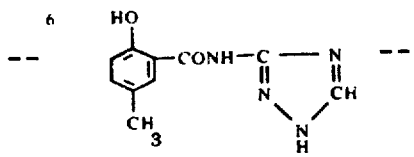

UNITED STATES PATENT OFFICE
CERTIFICATE OF CORRECTION

Patent No. 3,997,551  Dated December 14, 1976

Inventor(s) Motonobu Minagawa et al

It is certified that error appears in the above-identified patent and that said Letters Patent are hereby corrected as shown below:

Column 33, Example 9 :

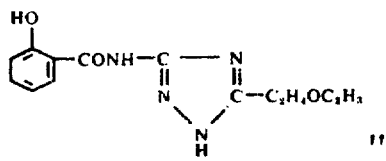

should be

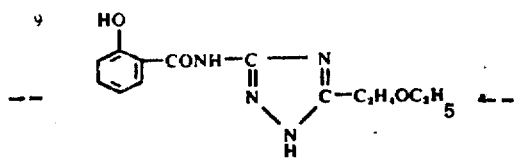

Column 35, Example 19 :

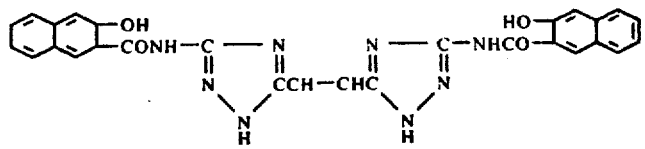

should be

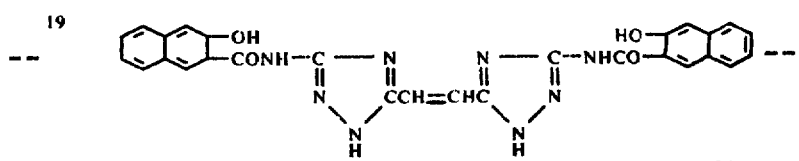

UNITED STATES PATENT OFFICE
CERTIFICATE OF CORRECTION

Patent No. 3,997,551  Dated December 14, 1976

Inventor(s) Motonobu Minagawa et al

It is certified that error appears in the above-identified patent and that said Letters Patent are hereby corrected as shown below:

Column 35, Example 21 :

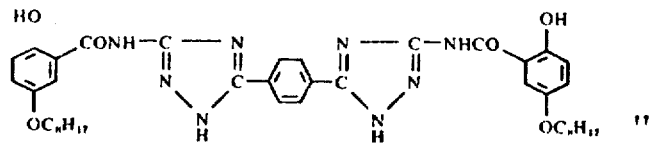

should be

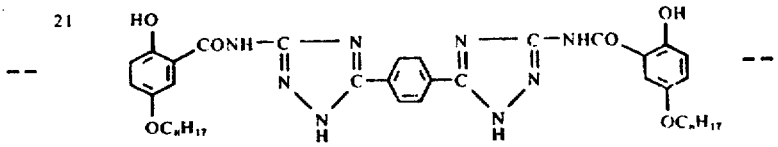

Column 36, Example 17 : "437" should be --487--

Oven Test Column:

Column 37, Example 22 :

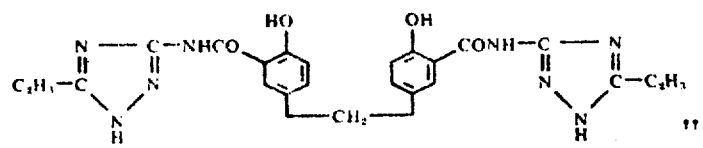

should be

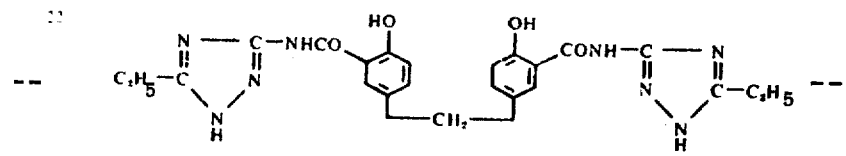

UNITED STATES PATENT OFFICE
CERTIFICATE OF CORRECTION

Patent No. 3,997,551    Dated December 14, 1976

Inventor(s) Motonobu Minagawa et al

It is certified that error appears in the above-identified patent and that said Letters Patent are hereby corrected as shown below:

Column 37, Example 26 : "26

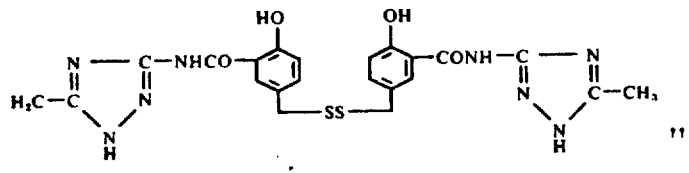

"

should be

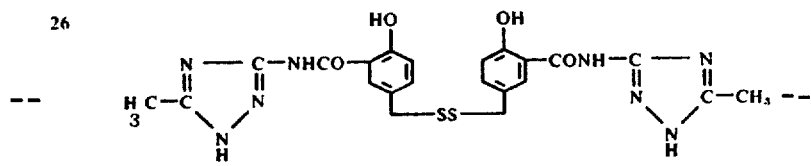

Example 27 : "27

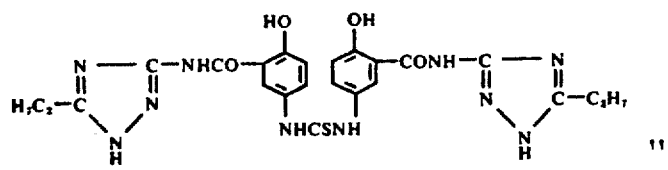

"

should be

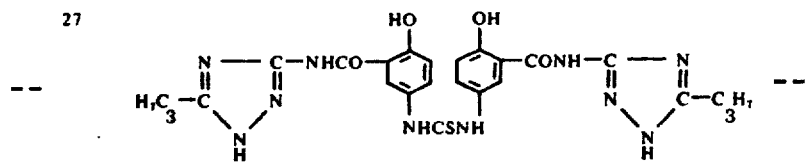

UNITED STATES PATENT OFFICE
CERTIFICATE OF CORRECTION

Patent No. 3,997,551  Dated December 14, 1976

Inventor(s) Motonobu Minagawa et al

It is certified that error appears in the above-identified patent and that said Letters Patent are hereby corrected as shown below:

Column 39, Example 31 :

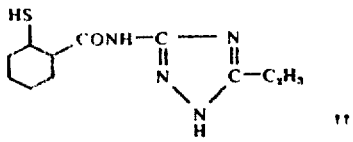

should be

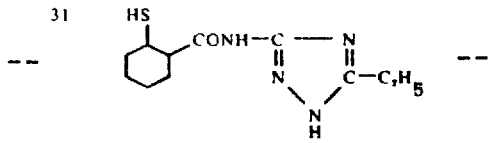

Column 39, line 65 : "saple" should be -- sample --

Column 41, line 66 : "C-O)" should be -- C=O) --

Column 44, line 45 : "as" should be -- was --

Column 46, line 14 : insert --where-- before "R₃"

Signed and Sealed this

Seventh Day of February 1978

[SEAL]

Attest:

RUTH C. MASON
Attesting Officer

LUTRELLE F. PARKER
Acting Commissioner of Patents and Trademarks